US006482628B1

(12) United States Patent
Poulose et al.

(10) Patent No.: US 6,482,628 B1
(45) **Date of Patent: *Nov. 19, 2002**

(54) MULTIPLY-SUBSTITUTED PROTEASE VARIANTS

(75) Inventors: Ayrookaran J. Poulose, Belmont; Volker Schellenberger, Palo Alto; James T. Kellis, Jr., Portola Valley; Christian Paech, Daly City; Joanne Nadherny; Donald P. Naki, both of San Francisco; Katherine D. Collier, Redwood City; Robert M. Caldwell, Belmont, all of CA (US); Andre C. Baeck, Bonheiden (BE)

(73) Assignee: Genencor International, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/178,173

(22) Filed: Oct. 23, 1998

Related U.S. Application Data

(63) Continuation-in-part of application No. 08/956,323, filed on Oct. 23, 1997, now abandoned, and a continuation-in-part of application No. 08/956,564, filed on Oct. 23, 1997, now abandoned, and a continuation-in-part of application No. 08/956,324, filed on Oct. 23, 1997, now abandoned.

(51) Int. Cl.[7] ............................ C12N 9/56; C12N 9/54; C12N 15/57; C12N 15/74; C11D 3/386

(52) U.S. Cl. ...................... 435/221; 435/69.1; 435/220; 435/252.31; 435/320.1; 435/471; 510/392; 536/23.2

(58) Field of Search ................................ 435/221, 222, 435/69.1, 471, 252.3, 320.1; 536/23.2

(56) References Cited

U.S. PATENT DOCUMENTS

| | | | | |
|---|---|---|---|---|
| 4,259,357 A | | 3/1981 | Van Kraneneburg ......... | 426/42 |
| 5,397,705 A | * | 3/1995 | Zukowski et al. .......... | 435/222 |
| 5,589,373 A | * | 12/1996 | Weiner et al. .............. | 435/220 |
| 5,665,587 A | * | 9/1997 | Aaslyng et al. ............. | 435/221 |
| 5,677,272 A | * | 10/1997 | Ghosh et al. ............... | 510/306 |
| 5,679,630 A | * | 10/1997 | Baeck et al. ................ | 510/305 |
| 5,985,639 A | * | 11/1999 | Christianson et al. ....... | 435/221 |

FOREIGN PATENT DOCUMENTS

| | | | |
|---|---|---|---|
| EP | 0 681 787 A | | 11/1995 |
| WO | WO 88 08165 A | | 10/1988 |
| WO | WO 91 00345 A | | 1/1991 |
| WO | WO 95 30010 A | | 11/1995 |
| WO | WO 95 30011 A | | 11/1995 |
| WO | WO 96/28556 A2 | * | 9/1996 |
| WO | WO 96 28566 A | | 9/1996 |

OTHER PUBLICATIONS

Ballinger, M. D. et al: "Designing Substilisin BPN to Cleave Substartes Containing Dibasic Residues" *Biochemistry*, vol. 34, No. 41, pp13312–13319 (1995).

* cited by examiner

*Primary Examiner*—Ponnathapu Achutamurthy
*Assistant Examiner*—William W. Moore
(74) *Attorney, Agent, or Firm*—Richard T. Ito

(57) ABSTRACT

Novel protease variants derived from the DNA sequences of naturally-occurring or recombinant non-human proteases are disclosed. The variant proteases, in general, are obtained by in vitro modification of a precursor DNA sequence encoding the naturally-occurring or recombinant protease to generate the substitution of a plurality of amino acid residues in the amino acid sequence of a precursor protease. Such variant proteases have properties which are different from those of the precursor protease, such as altered wash performance. The substituted amino acid residue correspond to positions 62, 212, 230, 232, 252 and 257 of *Bacillus amyloliquefaciens* subtilisin.

22 Claims, 7 Drawing Sheets

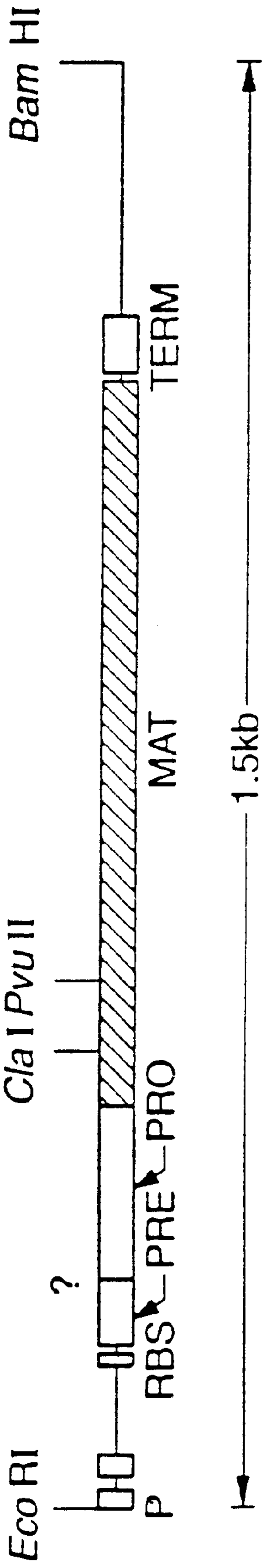
FIG._1A

⑤ P ③ ④ RBS -107 Met

1 GGTCTACTAAAATATTATTCCATACTATACAATTAATACACAGAATAATCTGTCTATTGGTTATTCTGCAAATGAAAAAAAGGAGAGGATAAAGA GTG

-100 PRE -90

Arg Gly Lys Lys Val Trp Ile Ser Leu Leu Phe Ala Leu Ala Leu Ile Phe Thr Met Ala Phe Gly Ser Thr Ser

99 AGA GGC AAA AAA GTA TGG ATC AGT TTG CTG TTT GCT TTA GCG TTA ATC TTT ACG ATG GCG TTC GGC AGC ACA TCC

-80 -70 PRO -60

Ser Ala Gln Ala Ala Gly Lys Ser Asn Gly Glu Lys Lys Tyr Ile Val Gly Phe Lys Gln Thr Met Ser Thr Met

174 TCT GCC CAG GCG GCA GGG AAA TCA AAC GGG GAA AAG AAA TAT ATT GTC GGG TTT AAA CAG ACA ATG AGC ACG ATG

-50 -40

Ser Ala Ala Lys Lys Lys Asp Val Ile Ser Glu Lys Gly Gly Lys Val Gln Lys Gln Phe Lys Tyr Val Asp Ala

249 AGC GCC GCT AAG AAG AAA GAT GTC ATT TCT GAA AAA GGC GGG AAA GTG CAA AAG CAA TTC AAA TAT GTA GAC GCA

-30 -20 -10

Ala Ser Ala Thr Leu Asn Glu Lys Ala Val Lys Glu Leu Lys Lys Asp Pro Ser Val Ala Tyr Val Glu Glu Asp

324 GCT TCA GCT ACA TTA AAC GAA AAA GCT GTA AAA GAA TTG AAA AAA GAC CCG AGC GTC GCT TAC GTT GAA GAA GAT

MAT

-1 1 10

His Val Ala His Ala Tyr Ala Gln Ser Val Pro Tyr Gly Val Ser Gln Ile Lys Ala Pro Ala Leu His Ser Gln

399 CAC GTA GCA CAT GCG TAC GCG CAG TCC GTG CCT TAC GGC GTA TCA CAA ATT AAA GCC CCT GCT CTG CAC TCT CAA 20 30 40

Gly Tyr Thr Gly Ser Asn Val Lys Val Ala Val Ile Asp Ser Gly Ile Asp Ser Ser His Pro Asp Leu Lys Val

474 GGC TAC ACT GGA TCA AAT GTT AAA GTA GCG GTT ATC GAC AGC GGT ATC GAT TCT TCT CAT CCT GAT TTA AAG GTA

FIG._1B - 1

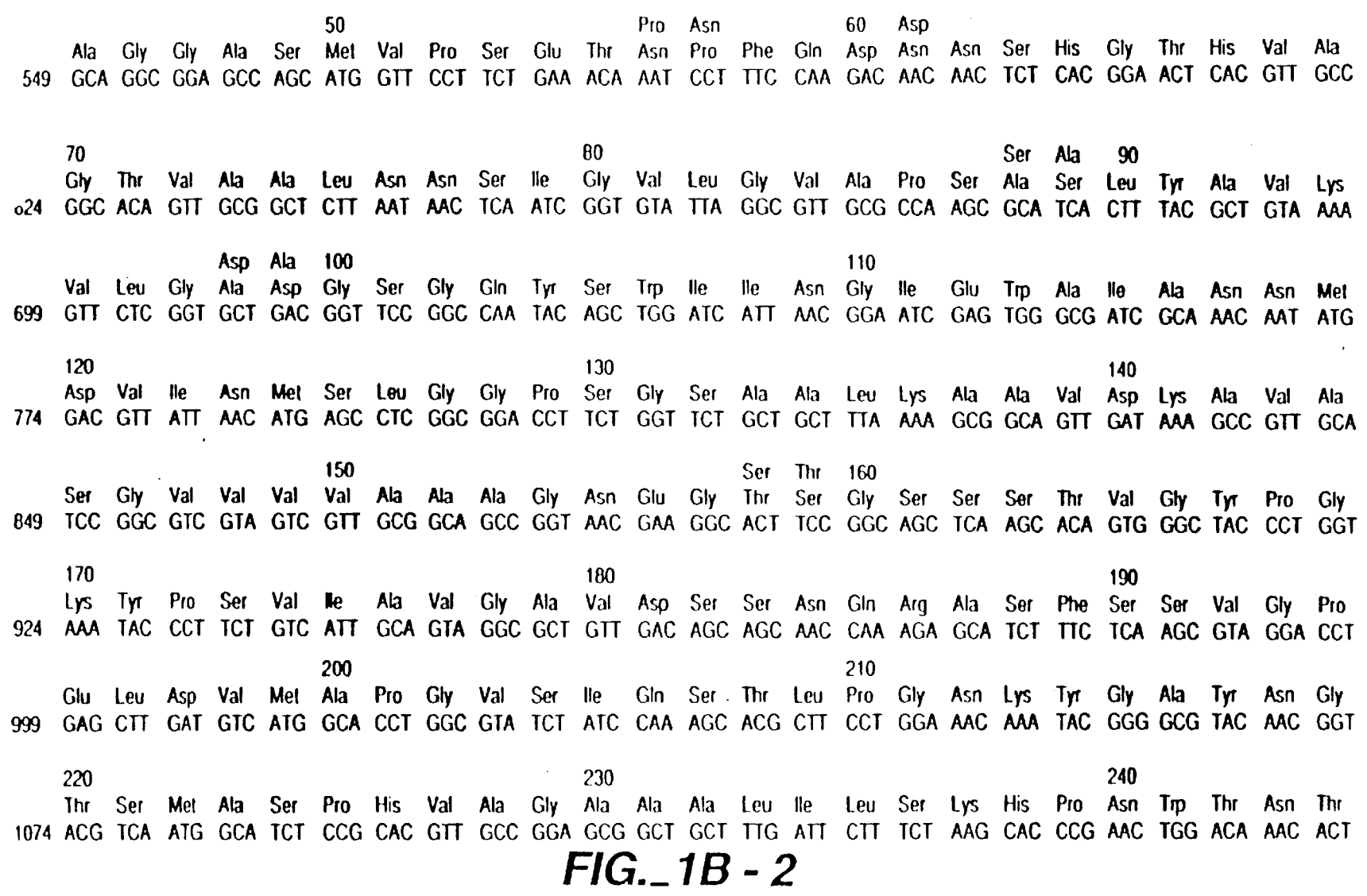

| | | | | | | | | | | | | | | | | | | | | | | | | | |
|---|---|---|---|---|---|---|---|---|---|---|---|---|---|---|---|---|---|---|---|---|---|---|---|---|---|
| | | | | | | 50 | | | | | | Pro | Asn | | | 60 | Asp | | | | | | | | |
| | Ala | Gly | Gly | Ala | Ser | Met | Val | Pro | Ser | Glu | Thr | Asn | Pro | Phe | Gln | Asp | Asn | Asn | Ser | His | Gly | Thr | His | Val | Ala |
| 549 | GCA | GGC | GGA | GCC | AGC | ATG | GTT | CCT | TCT | GAA | ACA | AAT | CCT | TTC | CAA | GAC | AAC | AAC | TCT | CAC | GGA | ACT | CAC | GTT | GCC |
| | 70 | | | | | | | | | | 80 | | | | | | | | Ser | Ala | 90 | | | | |
| | Gly | Thr | Val | Ala | Ala | Leu | Asn | Asn | Ser | Ile | Gly | Val | Leu | Gly | Val | Ala | Pro | Ser | Ala | Ser | Leu | Tyr | Ala | Val | Lys |
| 624 | GGC | ACA | GTT | GCG | GCT | CTT | AAT | AAC | TCA | ATC | GGT | GTA | TTA | GGC | GTT | GCG | CCA | AGC | GCA | TCA | CTT | TAC | GCT | GTA | AAA |
| | | | | Asp | Ala | 100 | | | | | | | | | | 110 | | | | | | | | | |
| | Val | Leu | Gly | Ala | Asp | Gly | Ser | Gly | Gln | Tyr | Ser | Trp | Ile | Ile | Asn | Gly | Ile | Glu | Trp | Ala | Ile | Ala | Asn | Asn | Met |
| 699 | GTT | CTC | GGT | GCT | GAC | GGT | TCC | GGC | CAA | TAC | AGC | TGG | ATC | ATT | AAC | GGA | ATC | GAG | TGG | GCG | ATC | GCA | AAC | AAT | ATG |
| | 120 | | | | | | | | | | 130 | | | | | | | | | | 140 | | | | |
| | Asp | Val | Ile | Asn | Met | Ser | Leu | Gly | Gly | Pro | Ser | Gly | Ser | Ala | Ala | Leu | Lys | Ala | Ala | Val | Asp | Lys | Ala | Val | Ala |
| 774 | GAC | GTT | ATT | AAC | ATG | AGC | CTC | GGC | GGA | CCT | TCT | GGT | TCT | GCT | GCT | TTA | AAA | GCG | GCA | GTT | GAT | AAA | GCC | GTT | GCA |
| | | | | | | 150 | | | | | | | | Ser | Thr | 160 | | | | | | | | | |
| | Ser | Gly | Val | Val | Val | Val | Ala | Ala | Ala | Gly | Asn | Glu | Gly | Thr | Ser | Gly | Ser | Ser | Ser | Thr | Val | Gly | Tyr | Pro | Gly |
| 849 | TCC | GGC | GTC | GTA | GTC | GTT | GCG | GCA | GCC | GGT | AAC | GAA | GGC | ACT | TCC | GGC | AGC | TCA | AGC | ACA | GTG | GGC | TAC | CCT | GGT |
| | 170 | | | | | | | | | | 180 | | | | | | | | | | 190 | | | | |
| | Lys | Tyr | Pro | Ser | Val | Ile | Ala | Val | Gly | Ala | Val | Asp | Ser | Ser | Asn | Gln | Arg | Ala | Ser | Phe | Ser | Ser | Val | Gly | Pro |
| 924 | AAA | TAC | CCT | TCT | GTC | ATT | GCA | GTA | GGC | GCT | GTT | GAC | AGC | AGC | AAC | CAA | AGA | GCA | TCT | TTC | TCA | AGC | GTA | GGA | CCT |
| | | | | | | 200 | | | | | | | | | | 210 | | | | | | | | | |
| | Glu | Leu | Asp | Val | Met | Ala | Pro | Gly | Val | Ser | Ile | Gln | Ser | Thr | Leu | Pro | Gly | Asn | Lys | Tyr | Gly | Ala | Tyr | Asn | Gly |
| 999 | GAG | CTT | GAT | GTC | ATG | GCA | CCT | GGC | GTA | TCT | ATC | CAA | AGC | ACG | CTT | CCT | GGA | AAC | AAA | TAC | GGG | GCG | TAC | AAC | GGT |
| | 220 | | | | | | | | | | 230 | | | | | | | | | | 240 | | | | |
| | Thr | Ser | Met | Ala | Ser | Pro | His | Val | Ala | Gly | Ala | Ala | Ala | Leu | Ile | Leu | Ser | Lys | His | Pro | Asn | Trp | Thr | Asn | Thr |
| 1074 | ACG | TCA | ATG | GCA | TCT | CCG | CAC | GTT | GCC | GGA | GCG | GCT | GCT | TTG | ATT | CTT | TCT | AAG | CAC | CCG | AAC | TGG | ACA | AAC | ACT |

FIG._1B - 2

```
                               250 Gln                                                 260
     Gln Val Arg Ser Ser Leu Glu Asn Thr Thr Thr Lys Leu Gly Asp Ser Phe Tyr Tyr Gly Lys Gly Leu Ile Asn
1149 CAA GTC CGC AGC AGT TTA GAA AAC ACC ACT ACA AAA CTT GGT GAT TCT TTC TAC TAT GGA AAA GGG CTG ATC AAC

     270                 275
     Val Gln Ala Ala Ala Gln OC                 TERM
1224 GTA CAG GCG GCA GCT CAG TAA AACATAAAAAACCGGCCTTGGCCCCGCCGGTTTTTTATTTTTCTTCCTCCGCATGTTCAATCCGCTCC

1316 ATAATCGACGGATGGCTCCCTCTGAAAATTTTAACGAGAAACGGCGGGTTGACCCGGCTCAGTCCCGTAACGGCCAAGTCCTGAAACGTCTCAATCGCCG

1416 CTTCCCGGTTTCCGGTCAGCTCAATGCCGTAACGGTCGGCGGCGTTTTCCTGATACCGGGAGACGGCATTCGTAATCGGATC
```

FIG._1B - 3

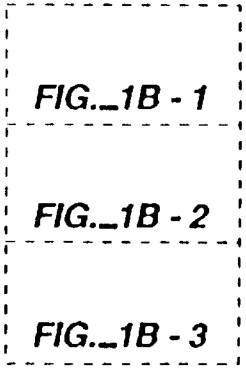

FIG._1B

CONSERVED RESIDUES IN SUBTILISINS FROM
*BACILLUS AMYLOLIQUEFACIENS*

```
1                 10                  20
A Q S V P . G . . . . . A P A . H . . G

21                30                  40
. T G S . V K V A V . D . G . . . . H P

41                50                  60
D L . . . G G A S . V P . . . . . . Q D

61                70                  80
. N . H G T H V A G T . A A L N N S I G

81                90                 100
V L G V A P S A . L Y A V K V L G A . G

101              110                 120
S G . . S . L . . G . E W A . N . . . .

121              130                 140
V . N . S L G . P S . S . . . . . A . .

141              150                 160
. . . . . G V . V V A A . G N . G . . .

161              170                 180
. . . . . . Y P . . Y . . . . A V G A .

181              190                 200
D . . N . . A S F S . . G . . L D . . A

201              210                 220
P G V . . Q S T . P G . . Y . . . N G T

221              230                 240
S M A . P H V A G A A A L . . . K . . .

241              250                 260
W . . . Q . R . . L . N T . . . L G . .

261              270
. . Y G . G L . N . . A A . .
```

COMPARISON OF SUBTILISIN SEQUENCES FROM:

*B.amyloliquefaciens*
*B.subtilis*
*B.licheniformis*
*B.lentus*

```
01                10                  20                  30
\ Q S V P Y G V S Q I K A P A L H S Q G Y T G S N V K V A V I D S G I D S S H P
A Q S V P Y G I S Q I K A P A L H S Q G Y T G S N V K V A V I D S G I D S S H P
A Q T V P Y G I P L I K A D K V Q A Q G F K G A N V K V A V L D T G I Q A S H P
A Q S V P W G I S R V Q A P A A H N R G L T G S G V K V A V L D T G I S T * H P

41                50                  60                  70
D L K V A G G A S M V P S E T N P F Q D N N S H G T H V A G T V A A L N N S I G
D L N V R G G A S F V P S E T N P Y Q D G S S H G T H V A G T I A A L N N S I G
D L N V V G G A S F V A G E A Y N * T D G N G H G T H V A G T V A A L D N T T G
D L N I R G G A S F V P G E * P S T Q D G N G H G T H V A G T I A A L N N S I G

81                90                  100                 110
V L G V A P S A S L Y A V K V L G A D G S G Q Y S W I I N G I E W A I A N N M D
V L G V S P S A S L Y A V K V L D S T G S G Q Y S W I I N G I E W A I S N N M D
  L G V A P S V S L Y A V K V L N S S G S G S Y S G I V S G I E W A T T N G M D
V L G V A P S A E L Y A V K V L G A S G S G S V S S I A Q G L E W A G N N G M H

121               130                 140                 150
V I N M S L G G P S G S A A L K A A V D K A V A S G V V V V A A A G N E G T S G
V I N M S L G G P T G S T A L K T V V D K A V S S G I V V A A A A G N E G S S G
V I N M S L G G A S G S T A M K Q A V D N A Y A R G V V V V A A A G N S G N S G
V A N L S L G S P S P S A T L E Q A V N S A T S R G V L V V A A S G N S G A G S
```

```
161                 170                      180                     190
S S S T V G Y P G K Y P S V I A V G A V D S S N Q R A S F S S V G P E L D V M A
S T S T V G Y P A K Y P S T I A V G A V N S S N Q R A S F S S A G S E L D V M A
S T N T I G Y P A K Y D S V I A V G A V D S N S N R A S F S S V G A E L E V M A
* * * * I S Y P A R Y A N A M A V G A T D Q N N N R A S F S Q Y G A G L D I V A

201                 210                      220                     230
P G V S I Q S T L P G N K Y G A Y N G T S M A S P H V A G A A A L I L S K H P N
P G V S I Q S T L P G G T Y G A Y N G T S M A T P H V A G A A A L I L S K H P T
P G A G V Y S T Y P T N T Y A T L N G T S M A S P H V A G A A A L I L S K H P N
P G V N V Q S T Y P G S T Y A S L N G T S M A T P H V A G A A A L V K Q K N P S

241                 250                      260                     270
W T N T Q V R S S L E N T T T K L G D S F Y Y G K G L I N V Q A A A Q
W T N A Q V R D R L E S T A T Y L G N S F Y Y G K G L I N V Q A A A Q
L S A S Q V R N R L S S T A T Y L G S S F Y Y G K G L I N V E A A A Q
W S N V Q I R N H L K N T A T S L G S T N L Y G S G L V N A E A A T R
```

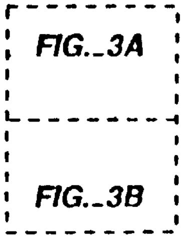

MULTIPLY-SUBSTITUTED PROTEASE VARIANTS

RELATED APPLICATIONS

The present application is a continuation-in-part application of U.S. patent application Ser. No. 08/956,323, filed Oct. 23, 1997, abandoned U.S. patent application Ser. No. 08/956,564, filed Oct. 23, 1997, abandoned and U.S. patent application Ser. No. 08/956,324 filed Oct. 23, 1997, abandoned all of which are hereby incorporated herein in their entirety.

BACKGROUND OF THE INVENTION

Serine proteases are a subgroup of carbonyl hydrolases. They comprise a diverse class of enzymes having a wide range of specificities and biological functions. Stroud, R. *Sci. Amer.*, 131:74–88. Despite their functional diversity, the catalytic machinery of serine proteases has been approached by at least two genetically distinct families of enzymes: 1) the subtilisins and 2) the mammalian chymotrypsin-related and homologous bacterial serine proteases (e.g., trypsin and S. gresius trypsin). These two families of serine proteases show remarkably similar mechanisms of catalysis. Kraut, J. (1977), *Annu. Rev. Biochem.*, 46:331–358. Furthermore, although the primary structure is unrelated, the tertiary structure of these two enzyme families bring together a conserved catalytic triad of amino acids consisting of serine, histidine and aspartate.

Subtilisins are serine proteases (approx. MW 27,500) which are secreted in large amounts from a wide variety of Bacillus species and other microorganisms. The protein sequence of subtilisin has been determined from at least nine different species of Bacillus. Markland, F. S., et al. (1983), *Hoppe-Seyler's Z. Physiol. Chem.*, 364:1537–1540. The three-dimensional crystallographic structure of subtilisins from *Bacillus amyloliquefaciens, Bacillus licheniforimis* and several natural variants of *B. lentus* have been reported. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972), *Biochemistry*, 11:2439–2449) or product complexes (Robertus, J. D., et al. (1976), *J. Biol. Chem.*, 251:1097–1103) have also provided information regarding the active site and putative substrate binding cleft of subtilisin. In addition, a large number of kinetic and chemical modification studies have been reported for subtilisin; Svendsen, B. (1976), *Carlsberg Res. Commun.*, 41:237–291; Markland, F. S. Id.) as well as at least one report wherein the side chain of methionine at residue 222 of subtilisin was converted by hydrogen peroxide to methionine-sulfoxide (Stauffer, D. C., et al. (1965), *J. Biol. Chem.*, 244:5333–5338) and extensive site-specific mutagenesis has been carried out (Wells and Estell (1988) *TIBS* 13:291–297)

SUMMARY OF THE INVENTION

It is an object herein to provide a protease variant containing a substitution of an amino acid at one or more residue positions corresponding to residue positions selected from the group consisting of 62, 212, 230, 232, 252 and 257 of *Bacillus amyloliquefaciens* subtilisin.

While any combination of the above listed amino acid substitutions may be employed, the preferred protease variant enzymes of the present invention comprise the substitution of amino acid residues in the following combinations.

All of the residue positions correspond to positions of *Bacillus amyloliquefaciens* subtilisin:

(1) a protease variant including substitutions of the amino acid residues at position 62 and at one or more of the following positions 103, 104, 109, 159, 213, 232, 236, 245, 248 and 252;

(2) a protease variant including substitutions of the amino acid residues at position 212 and at one or more of the following positions 12, 98, 102, 103, 104, 159, 232, 236, 245, 248 and 252;

(3) a protease variant including substitutions of the amino acid residues at position 230 and at one or more of the following positions 68, 103, 104, 159, 232, 236 and 245;

(4) a protease variant including substitutions of the amino acid residues at position 232 and at one or more of the following positions: 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(5) a protease variant including substitutions of the amino acid residues at position 232 and at one or more of the following positions 103, 104, 236 and 245;

(6) a protease variant including substitutions of the amino acid residues at position 232 and 103 and at one or more of the following positions 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(7) a protease variant including substitutions of the amino acid residues at position 232 and 104 and at one or more of the following positions 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(8) a protease variant including substitutions of the amino acid residues at position 232 and 236 and at one or more of the following positions 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(9) a protease variant including substitutions of the amino acid residues at position 232 and 245 and at one or more of the following positions 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(10) a protease variant including substitutions of the amino acid residues at position 232, 103, 104, 236 and 245 and at one or more of the following positions 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(11) a protease variant including substitutions of the amino acid residues at position 252 and at one or more of the following positions 1, 9, 12, 61, 62, 68, 97, 98, 101, 102, 103, 104, 109, 130, 131, 159, 183, 185, 210, 212, 213, 217, 232, 236, 245, 248 and 270;

(12) a protease variant including substitutions of the amino acid residues at position 252 and at one or more of the following positions 103, 104, 236 and 245;

(13) a protease variant including substitutions of the amino acid residues at positions 252 and 103 and at one or more of the following positions 1, 9, 12, 61, 62, 68, 97, 98, 101, 102, 103, 104, 109, 130, 131, 159, 183, 185, 210, 212, 213, 217, 232, 236, 245, 248 and 270;

(14) a protease variant including substitutions of the amino acid residues at positions 252 and 104 and at one or more of the following positions 1, 9, 12, 61, 62, 68, 97, 98, 101, 102, 103, 104, 109, 130, 131, 159, 183, 185, 210, 212, 213, 217, 232, 236, 245, 248 and 270;

(15) a protease variant including substitutions of the amino acid residues at positions 252 and 236 and at one or more of the following positions 1, 9, 12, 61, 62, 68, 97, 98, 101, 102, 103, 104, 109, 130, 131, 159, 183, 185, 210, 212, 213, 217, 232, 236, 245, 248 and 270;

(16) a protease variant including substitutions of the amino acid residues at positions 252 and 245 and at one or more of the following positions 1, 9, 12, 61, 62, 68, 97, 98, 101, 102, 103, 104, 109, 130, 131, 159, 183, 185, 210, 212, 213, 217, 232, 236, 245, 248 and 270;

(17) a protease variant including substitutions of the amino acid residues at positions 252, 103, 104, 236 and 245 and at one or more of the following positions 1, 9, 12, 61, 62, 68, 97, 98, 101, 102, 103, 104, 109, 130, 131, 159, 183, 185, 210, 212, 213, 217, 232, 236, 245, 248 and 270; and

(18) a protease variant including substitutions of the amino acid residues at position 257 and at one or more of the following positions 68, 103, 104, 205, 209, 210, 232, 236, 245 and 275. More preferred protease variants are substitution sets selected from the group consisting of residue positions corresponding to positions in Table 1 of Bacillus amyloliquefaciens subtilisin:

TABLE 1

| | | | | | | | | | |
|---|---|---|---|---|---|---|---|---|---|
| 76 | 103 | 104 | 212 | 271 | | | | | |
| 76 | 103 | 104 | 252 | 261 | | | | | |
| 76 | 103 | 104 | 212 | 258 | | | | | |
| 4 | 76 | 103 | 104 | 159 | 217 | 252 | | | |
| 12 | 62 | 76 | 103 | 104 | 159 | | | | |
| 76 | 103 | 104 | 212 | 268 | 271 | | | | |
| 76 | 87 | 103 | 104 | 212 | 271 | | | | |
| 76 | 103 | 104 | 212 | 245 | 271 | | | | |
| 76 | 103 | 104 | 134 | 141 | 212 | 271 | | | |
| 76 | 103 | 104 | 212 | 236 | 243 | 271 | | | |
| 20 | 62 | 76 | 103 | 104 | | | | | |
| 68 | 76 | 103 | 104 | 159 | 232 | 236 | 245 | | |
| 76 | 103 | 104 | 232 | 245 | | | | | |
| 24 | 68 | 76 | 103 | 104 | 159 | 232 | 236 | 245 | |
| 68 | 103 | 104 | 159 | 232 | 236 | 245 | 252 | | |
| 68 | 76 | 103 | 104 | 159 | 213 | 232 | 236 | 245 | 260 |
| 68 | 103 | 104 | 159 | 232 | 236 | 245 | 248 | 252 | |
| 68 | 103 | 104 | 159 | 232 | 236 | 245 | | | |
| 68 | 103 | 104 | 140 | 159 | 232 | 236 | 245 | 252 | |
| 43 | 68 | 103 | 104 | 159 | 232 | 236 | 245 | 252 | |
| 43 | 68 | 103 | 104 | 159 | 232 | 236 | 245 | | |
| 43 | 68 | 103 | 104 | 159 | 232 | 236 | 245 | 252 | |
| 68 | 87 | 103 | 104 | 159 | 232 | 236 | 245 | 252 | 275 |
| 68 | 103 | 104 | 159 | 232 | 236 | 245 | 257 | | |
| 68 | 103 | 104 | 116 | 159 | 232 | 236 | 245 | | |
| 68 | 103 | 104 | 159 | 232 | 236 | 245 | 248 | | |
| 10 | 68 | 103 | 104 | 159 | 232 | 236 | 245 | | |
| 68 | 103 | 104 | 159 | 203 | 232 | 236 | 245 | | |
| 68 | 103 | 104 | 159 | 232 | 236 | 237 | 245 | | |
| 68 | 76 | 79 | 103 | 104 | 159 | 232 | 236 | 245 | |
| 68 | 103 | 104 | 159 | 183 | 232 | 236 | 245 | | |
| 68 | 103 | 104 | 159 | 174 | 206 | 232 | 236 | 245 | |
| 68 | 103 | 104 | 159 | 188 | 232 | 236 | 245 | | |
| 68 | 103 | 104 | 159 | 230 | 232 | 236 | 245 | | |
| 68 | 98 | 103 | 104 | 159 | 232 | 236 | 245 | | |
| 68 | 103 | 104 | 159 | 215 | 232 | 236 | 245 | | |
| 68 | 103 | 104 | 159 | 232 | 236 | 245 | 248 | | |
| 68 | 76 | 103 | 104 | 159 | 232 | 236 | 245 | | |
| 68 | 76 | 103 | 104 | 159 | 210 | 232 | 236 | 245 | |
| 68 | 76 | 103 | 104 | 159 | 232 | 236 | 245 | 257 | |
| 76 | 103 | 104 | 232 | 236 | 245 | 257 | | | |
| 68 | 103 | 104 | 159 | 232 | 236 | 245 | 257 | 275 | |
| 76 | 103 | 104 | 257 | 275 | | | | | |
| 68 | 103 | 104 | 159 | 224 | 232 | 236 | 245 | 257 | |
| 76 | 103 | 104 | 159 | 232 | 236 | 245 | 257 | | |
| 68 | 76 | 103 | 104 | 159 | 209 | 232 | 236 | 245 | |
| 68 | 76 | 103 | 104 | 159 | 211 | 232 | 236 | 245 | |
| 12 | 68 | 76 | 103 | 104 | 159 | 214 | 232 | 236 | 245 |
| 68 | 76 | 103 | 104 | 159 | 215 | 232 | 236 | 245 | |
| 12 | 68 | 76 | 103 | 104 | 159 | 232 | 236 | 245 | |
| 20 | 68 | 76 | 103 | 104 | 159 | 232 | 236 | 245 | 259 |
| 68 | 87 | 76 | 103 | 104 | 159 | 232 | 236 | 245 | 260 |
| 68 | 76 | 103 | 104 | 159 | 232 | 236 | 245 | 261 | |
| 76 | 103 | 104 | 232 | 236 | 242 | 245 | | | |
| 68 | 76 | 103 | 104 | 159 | 210 | 232 | 236 | 245 | |
| 12 | 48 | 68 | 76 | 103 | 104 | 159 | 232 | 236 | 245 |
| 76 | 103 | 104 | 232 | 236 | 245 | | | | |
| 76 | 103 | 104 | 159 | 192 | 232 | 236 | 245 | | |
| 76 | 103 | 104 | 147 | 159 | 232 | 236 | 245 | 248 | 251 |

TABLE 1-continued

| | | | | | | | | | | | |
|---|---|---|---|---|---|---|---|---|---|---|---|
| 12 | 68 | 76 | 103 | 104 | 159 | 232 | 236 | 245 | 272 | | |
| 68 | 76 | 103 | 104 | 159 | 183 | 206 | 232 | 236 | 245 | | |
| 68 | 76 | 103 | 104 | 159 | 232 | 236 | 245 | 256 | | | |
| 68 | 76 | 103 | 104 | 159 | 206 | 232 | 236 | 245 | | | |
| 27 | 68 | 76 | 103 | 104 | 159 | 232 | 236 | 245 | | | |
| 68 | 76 | 103 | 104 | 116 | 159 | 170 | 185 | 232 | 236 | 245 | |
| 61 | 68 | 103 | 104 | 159 | 232 | 236 | 245 | 248 | 252 | | |
| 43 | 68 | 103 | 104 | 159 | 232 | 236 | 245 | 248 | 252 | | |
| 68 | 103 | 104 | 159 | 212 | 232 | 236 | 245 | 248 | 252 | | |
| 68 | 103 | 104 | 99 | 159 | 184 | 232 | 236 | 245 | 248 | 252 | |
| 103 | 104 | 159 | 232 | 236 | 245 | 248 | 252 | | | | |
| 68 | 103 | 104 | 159 | 209 | 232 | 236 | 245 | 248 | 252 | | |
| 68 | 103 | 104 | 109 | 159 | 232 | 236 | 245 | 248 | 252 | | |
| 20 | 68 | 103 | 104 | 159 | 232 | 236 | 245 | 248 | 252 | | |
| 68 | 103 | 104 | 159 | 209 | 232 | 236 | 245 | 248 | 252 | | |
| 68 | 103 | 104 | 159 | 232 | 236 | 245 | 248 | 252 | 261 | | |
| 68 | 103 | 104 | 159 | 185 | 232 | 236 | 245 | 248 | 252 | | |
| 68 | 103 | 104 | 159 | 210 | 232 | 236 | 245 | 248 | 252 | | |
| 68 | 103 | 104 | 159 | 185 | 210 | 232 | 236 | 245 | 248 | 252 | |
| 68 | 103 | 104 | 159 | 212 | 232 | 236 | 245 | 248 | 252 | | |
| 68 | 103 | 104 | 159 | 213 | 232 | 236 | 245 | 248 | 252 | | |
| 68 | 103 | 104 | 213 | 232 | 236 | 245 | 248 | 252 | | | |
| 68 | 103 | 104 | 159 | 215 | 232 | 236 | 245 | 248 | 252 | | |
| 68 | 103 | 104 | 159 | 216 | 232 | 236 | 245 | 248 | 252 | | |
| 20 | 68 | 103 | 104 | 159 | 232 | 236 | 245 | 248 | 252 | | |
| 68 | 103 | 104 | 159 | 173 | 232 | 236 | 245 | 248 | 252 | | |
| 68 | 103 | 104 | 159 | 232 | 236 | 245 | 248 | 251 | 252 | | |
| 68 | 103 | 104 | 159 | 206 | 232 | 236 | 245 | 248 | 252 | | |
| 68 | 103 | 104 | 159 | 232 | 236 | 245 | 248 | 252 | | | |
| 55 | 68 | 103 | 104 | 159 | 232 | 236 | 245 | 248 | 252 | | |
| 68 | 103 | 104 | 159 | 232 | 236 | 245 | 248 | 252 | 255 | | |
| 68 | 103 | 104 | 159 | 232 | 236 | 245 | 248 | 252 | 256 | | |
| 68 | 103 | 104 | 159 | 232 | 236 | 245 | 248 | 252 | 260 | | |
| 68 | 103 | 104 | 159 | 232 | 236 | 245 | 248 | 252 | 257 | | |
| 68 | 103 | 104 | 159 | 232 | 236 | 245 | 248 | 252 | 258 | | |
| 8 | 68 | 103 | 104 | 159 | 232 | 236 | 245 | 248 | 252 | 269 | |
| 68 | 103 | 104 | 116 | 159 | 232 | 236 | 245 | 248 | 252 | 260 | |
| 68 | 103 | 104 | 159 | 232 | 236 | 245 | 248 | 252 | 261 | | |
| 68 | 103 | 104 | 159 | 232 | 236 | 245 | 248 | 252 | 261 | | |
| 68 | 76 | 103 | 104 | 159 | 232 | 236 | 245 | 248 | 252 | | |
| 68 | 103 | 104 | 232 | 236 | 245 | 248 | 252 | | | | |
| 103 | 104 | 159 | 232 | 236 | 245 | 248 | 252 | | | | |
| 68 | 103 | 104 | 159 | 232 | 236 | 245 | 248 | 252 | | | |
| 18 | 68 | 103 | 104 | 159 | 232 | 236 | 245 | 248 | 252 | | |
| 68 | 103 | 104 | 159 | 232 | 236 | 245 | 248 | 252 | | | |
| 68 | 76 | 101 | 103 | 104 | 159 | 213 | 218 | 232 | 236 | 245 | 260 |
| 68 | 103 | 104 | 159 | 228 | 232 | 236 | 245 | 248 | 252 | | |
| 33 | 68 | 76 | 103 | 104 | 159 | 232 | 236 | 245 | 248 | 252 | |
| 68 | 76 | 89 | 103 | 104 | 159 | 210 | 213 | 232 | 236 | 245 | 260 |
| 61 | 68 | 76 | 103 | 104 | 159 | 232 | 236 | 245 | 248 | 252 | |
| 103 | 104 | 159 | 205 | 210 | 232 | 236 | 245 | | | | |
| 61 | 68 | 103 | 104 | 130 | 159 | 232 | 236 | 245 | 248 | 252 | |
| 61 | 68 | 103 | 104 | 133 | 137 | 159 | 232 | 236 | 245 | 248 | 252 |
| 61 | 103 | 104 | 133 | 159 | 232 | 236 | 245 | 248 | 252 | | |
| 68 | 103 | 104 | 159 | 232 | 236 | 245 | 248 | 252 | | | |
| 68 | 103 | 104 | 159 | 218 | 232 | 236 | 245 | 248 | 252 | | |
| 61 | 68 | 103 | 104 | 159 | 160 | 232 | 236 | 245 | 248 | 252 | |
| 3 | 61 | 68 | 76 | 103 | 104 | 232 | 236 | 245 | 248 | 252 | |
| 61 | 68 | 103 | 104 | 159 | 167 | 232 | 236 | 245 | 248 | 252 | |
| 97 | 103 | 104 | 159 | 232 | 236 | 245 | 248 | 252 | | | |
| 98 | 103 | 104 | 159 | 232 | 236 | 245 | 248 | 252 | | | |
| 99 | 103 | 104 | 159 | 232 | 236 | 245 | 248 | 252 | | | |
| 101 | 103 | 104 | 159 | 232 | 236 | 245 | 248 | 252 | | | |
| 102 | 103 | 104 | 159 | 232 | 236 | 245 | 248 | 252 | | | |
| 103 | 104 | 106 | 159 | 232 | 236 | 245 | 248 | 252 | | | |
| 103 | 104 | 109 | 159 | 232 | 236 | 245 | 248 | 252 | | | |
| 103 | 104 | 159 | 232 | 236 | 245 | 248 | 252 | 261 | | | |
| 62 | 103 | 104 | 159 | 232 | 236 | 245 | 248 | 252 | | | |
| 103 | 104 | 159 | 184 | 232 | 236 | 245 | 248 | 252 | | | |
| 103 | 104 | 159 | 166 | 232 | 236 | 245 | 248 | 252 | | | |
| 103 | 104 | 159 | 217 | 232 | 236 | 245 | 248 | 252 | | | |
| 20 | 62 | 103 | 104 | 159 | 213 | 232 | 236 | 245 | 248 | 252 | |
| 62 | 103 | 104 | 159 | 213 | 232 | 236 | 245 | 248 | 252 | | |
| 103 | 104 | 159 | 206 | 217 | 232 | 236 | 245 | 248 | 252 | | |
| 62 | 103 | 104 | 159 | 206 | 232 | 236 | 245 | 248 | 252 | | |
| 103 | 104 | 130 | 159 | 232 | 236 | 245 | 248 | 252 | | | |
| 103 | 104 | 131 | 159 | 232 | 236 | 245 | 248 | 252 | | | |
| 27 | 103 | 104 | 159 | 232 | 236 | 245 | 248 | 252 | | | |
| 38 | 103 | 104 | 159 | 232 | 236 | 245 | 248 | 252 | | | |

TABLE 1-continued

| | | | | | | | | | | | |
|---|---|---|---|---|---|---|---|---|---|---|---|
| 38 | 76 | 103 | 104 | 159 | 213 | 232 | 236 | 245 | 260 | | |
| 68 | 76 | 103 | 104 | 159 | 213 | 232 | 236 | 245 | 260 | 271 | |
| 68 | 76 | 103 | 104 | 159 | 209 | 213 | 232 | 236 | 245 | 260 | |
| 68 | 76 | 103 | 104 | 159 | 210 | 213 | 232 | 236 | 245 | 260 | |
| 68 | 76 | 103 | 104 | 159 | 205 | 213 | 232 | 236 | 245 | 260 | |
| 68 | 76 | 103 | 104 | 159 | 210 | 232 | 236 | 245 | 260 | | |
| 68 | 103 | 104 | 159 | 213 | 232 | 236 | 245 | 260 | | | |
| 76 | 103 | 104 | 159 | 213 | 232 | 236 | 245 | 260 | | | |
| 68 | 103 | 104 | 159 | 209 | 232 | 236 | 245 | | | | |
| 68 | 103 | 104 | 159 | 210 | 232 | 236 | 245 | | | | |
| 68 | 103 | 104 | 159 | 230 | 232 | 236 | 245 | | | | |
| 68 | 103 | 104 | 159 | 126 | 232 | 236 | 245 | | | | |
| 68 | 103 | 104 | 159 | 205 | 232 | 236 | 245 | | | | |
| 68 | 103 | 104 | 159 | 210 | 232 | 236 | 245 | | | | |
| 103 | 104 | 159 | 230 | 236 | 245 | | | | | | |
| 68 | 103 | 104 | 159 | 232 | 236 | 245 | 260 | | | | |
| 103 | 104 | 159 | 232 | 236 | 245 | | | | | | |
| 68 | 103 | 104 | 159 | 174 | 232 | 236 | 245 | 257 | | | |
| 68 | 103 | 104 | 159 | 194 | 232 | 236 | 245 | 257 | | | |
| 68 | 103 | 104 | 159 | 209 | 232 | 236 | 245 | 257 | | | |
| 103 | 104 | 159 | 232 | 236 | 245 | 257 | | | | | |
| 68 | 76 | 103 | 104 | 159 | 213 | 232 | 236 | 245 | 260 | 261 | |
| 68 | 103 | 104 | 159 | 232 | 236 | 245 | 257 | 261 | | | |
| 103 | 104 | 159 | 213 | 232 | 236 | 245 | 260 | | | | |
| 103 | 104 | 159 | 210 | 232 | 236 | 245 | 248 | 252 | | | |
| 103 | 104 | 159 | 209 | 232 | 236 | 245 | 257 | | | | |
| 68 | 76 | 103 | 104 | 159 | 210 | 213 | 232 | 236 | 245 | 260 | |
| 12 | 103 | 104 | 159 | 209 | 213 | 232 | 236 | 245 | 260 | | |
| 103 | 104 | 209 | 232 | 236 | 245 | 257 | | | | | |
| 103 | 104 | 159 | 205 | 210 | 213 | 232 | 236 | 245 | 260 | | |
| 103 | 104 | 159 | 205 | 209 | 232 | 236 | 245 | 260 | | | |
| 68 | 103 | 104 | 159 | 205 | 209 | 210 | 232 | 236 | 245 | | |
| 103 | 104 | 159 | 205 | 209 | 210 | 232 | 236 | 245 | 257 | | |
| 103 | 104 | 159 | 205 | 209 | 232 | 236 | 245 | 257 | | | |
| 68 | 103 | 104 | 159 | 205 | 209 | 210 | 232 | 236 | 245 | 260 | |
| 103 | 104 | 159 | 205 | 209 | 210 | 232 | 236 | 245 | | | |
| 103 | 104 | 159 | 209 | 210 | 232 | 236 | 245 | | | | |
| 103 | 104 | 159 | 205 | 210 | 232 | 236 | 245 | | | | |
| 68 | 103 | 104 | 128 | 159 | 232 | 236 | 245 | | | | |
| 48 | 103 | 104 | 159 | 230 | 236 | 245 | | | | | |
| 48 | 68 | 103 | 104 | 159 | 209 | 232 | 236 | 245 | | | |
| 48 | 68 | 103 | 104 | 159 | 232 | 236 | 245 | 248 | 252 | | |
| 48 | 68 | 103 | 104 | 159 | 232 | 236 | 245 | 257 | 261 | | |
| 102 | 103 | 104 | 159 | 212 | 232 | 236 | 245 | 248 | 252 | | |
| 12 | 102 | 103 | 104 | 159 | 212 | 232 | 236 | 245 | 248 | 252 | |
| 101 | 102 | 103 | 104 | 159 | 212 | 232 | 236 | 245 | 248 | 252 | |
| 98 | 102 | 103 | 104 | 159 | 212 | 232 | 236 | 245 | 248 | 252 | |
| 102 | 103 | 104 | 159 | 213 | 232 | 236 | 245 | 248 | 252 | | |
| 103 | 104 | 131 | 159 | 232 | 236 | 245 | 248 | 252 | | | |
| 103 | 104 | 159 | 184 | 232 | 236 | 245 | 248 | 252 | | | |
| 103 | 104 | 159 | 232 | 236 | 244 | 245 | 248 | 252 | | | |
| 62 | 103 | 104 | 159 | 213 | 232 | 236 | 245 | 248 | 252 | 256 | |
| 12 | 62 | 103 | 104 | 159 | 213 | 232 | 236 | 245 | 248 | 252 | |
| 101 | 103 | 104 | 159 | 185 | 232 | 236 | 245 | 248 | 252 | | |
| 101 | 103 | 104 | 159 | 206 | 232 | 236 | 245 | 248 | 252 | | |
| 101 | 103 | 104 | 159 | 213 | 232 | 236 | 245 | 248 | 252 | | |
| 98 | 102 | 103 | 104 | 159 | 232 | 236 | 245 | 248 | 252 | | |
| 101 | 102 | 103 | 104 | 159 | 232 | 236 | 245 | 248 | 252 | | |
| 98 | 102 | 103 | 104 | 159 | 212 | 232 | 236 | 245 | 248 | 252 | |
| 98 | 102 | 103 | 104 | 159 | 212 | 232 | 236 | 248 | 252 | | |
| 62 | 103 | 104 | 109 | 159 | 213 | 232 | 236 | 245 | 248 | 252 | |
| 62 | 103 | 104 | 159 | 212 | 213 | 232 | 236 | 245 | 248 | 252 | |
| 62 | 101 | 103 | 104 | 159 | 212 | 213 | 232 | 236 | 245 | 248 | 252 |
| 103 | 104 | 159 | 232 | 245 | 248 | 252 | | | | | |
| 103 | 104 | 159 | 230 | 245 | | | | | | | |
| 62 | 103 | 104 | 130 | 159 | 213 | 232 | 236 | 245 | 248 | 252 | |
| 101 | 103 | 104 | 130 | 159 | 232 | 236 | 245 | 248 | 252 | | |
| 101 | 103 | 104 | 128 | 159 | 232 | 236 | 245 | 248 | 252 | | |
| 62 | 101 | 103 | 104 | 159 | 213 | 232 | 236 | 245 | 248 | 252 | |
| 62 | 103 | 104 | 128 | 159 | 213 | 232 | 236 | 245 | 248 | 252 | |
| 62 | 103 | 104 | 128 | 159 | 213 | 232 | 236 | 245 | 248 | 252 | |
| 101 | 103 | 104 | 159 | 232 | 236 | 245 | 248 | 252 | 260 | | |
| 101 | 103 | 104 | 131 | 159 | 232 | 236 | 245 | 248 | 252 | | |
| 98 | 101 | 103 | 104 | 159 | 232 | 236 | 245 | 248 | 252 | | |
| 99 | 101 | 103 | 104 | 159 | 232 | 236 | 245 | 248 | 252 | | |
| 101 | 103 | 104 | 159 | 212 | 232 | 236 | 245 | 248 | 252 | | |
| 101 | 103 | 104 | 159 | 209 | 232 | 236 | 245 | 248 | 252 | | |
| 101 | 103 | 104 | 159 | 210 | 232 | 236 | 245 | 248 | 252 | | |
| 101 | 103 | 104 | 159 | 205 | 232 | 236 | 245 | 248 | 252 | | |

TABLE 1-continued

| | | | | | | | | | | | | |
|---|---|---|---|---|---|---|---|---|---|---|---|---|
| 101 | 103 | 104 | 159 | 230 | 236 | 245 | | | | | | |
| 101 | 103 | 104 | 159 | 194 | 232 | 236 | 245 | 248 | 252 | | | |
| 76 | 101 | 103 | 104 | 159 | 194 | 232 | 236 | 245 | 248 | 252 | | |
| 101 | 103 | 104 | 159 | 230 | 232 | 236 | 245 | 248 | 252 | | | |
| 62 | 103 | 104 | 159 | 185 | 206 | 213 | 232 | 236 | 245 | 248 | 252 | 271 |

Most preferred protease variants are substitution sets selected from the group consisting of residue positions corresponding to positions in Table 2 of *Bacillus amyloliquefaciens* subtilisin:

TABLE 2

| | | | | | | | | | |
|---|---|---|---|---|---|---|---|---|---|
| N76D | S103A | V1041 | S212P | E271V | | | | | |
| N76D | S103A | V1041 | N252K | N261Y | | | | | |
| N76D | S103A | V1041 | S212P | G258R | | | | | |
| V4E | N76D | S103A | V1041 | G159D | L217E | N252D | | | |
| Q12H | N62H | N76D | S103A | V1041 | G159D | | | | |
| N76D | S103A | V1041 | S212P | V268F | E271V | | | | |
| N76D | S87R | S103A | V1041 | 5212P | E271V | | | | |
| N76D | S103A | V1041 | S212P | 0245L | E271V | | | | |
| N76D | S103A | V1041 | T134S | 5141N | S212P | E271V | | | |
| N76D | S103A | V1041 | S212P | Q236L | N243S | E271V | | | |
| G20V | N62S | N76D | S103A | V1041 | | | | | |
| V68A | N76D | S103A | V1041 | G159D | A232V | Q236H | Q245R | | |
| N76D | S103A | V1041 | A232V | Q245R | | | | | |
| 524T | V68A | N76D | S103A | V1041 | G159D | A232V | Q236H | Q245R | |
| V68A | S103A | V1041 | G159D | A232V | Q236H | Q245R | N252K | | |
| V68A | N76D | S103A | V1041 | G159D | T213R | A232V | Q236H | Q245R | T260A |
| V68A | S103A | V1041 | G159D | A232V | Q236H | Q245R | N248D | N252K | |
| V68A | S103A | V1041 | G159D | A232V | Q236H | Q245R | | | |
| V68A | S103A | V1041 | N140D | G159D | A232V | Q236H | Q245R | N252K | |
| N43S | V68A | S103A | V1041 | G159D | A232V | Q236H | Q245R | N252K | |
| N43K | V68A | S103A | V1041 | G159D | A232V | Q236H | Q245R | | |
| N43D | V68A | S103A | V1041 | G159D | A232V | Q236H | Q245R | N252K | |
| V68A | S87G | S103A | V1041 | G159D | A232V | Q236H | Q245R | N252K | R275S |
| V68A | S103A | V1041 | G159D | A232V | Q236H | Q245R | L257V | | |
| V68A | S103A | V1041 | N116D | G159D | A232V | Q236H | Q245R | | |
| V68A | S103A | V1041 | G159D | A232V | Q236H | Q245R | N248D | | |
| R10C | V68A | S103A | V1041 | G159D | A232V | Q236H | Q245R | | |
| V68A | S103A | V1041 | G159D | V203E | A232V | Q236H | Q245R | | |
| V68A | S103A | V1041 | G159D | A232V | Q236H | K237E | Q245R | | |
| V68A | N76D | I79N | S103A | V1041 | G159D | A232V | Q236H | Q245R | |
| V68A | S103A | V1041 | G159D | N183D | A232V | Q236H | Q245R | | |
| V68A | S103A | V1041 | G159D | A174V | Q206L | A232V | Q236H | Q245R | |
| V68A | S103A | V1041 | G159D | S188C | A232V | Q236H | Q245R | | |
| V68A | S103A | V1041 | G159D | A230T | A232V | Q236H | Q245R | | |
| V68A | A98T | S103A | V1041 | G159D | A232V | Q236H | Q245R | | |
| V68A | S103A | V1041 | G159D | A215T | A232V | Q236H | Q245R | | |
| V68A | S103A | V1041 | GIS9D | A232V | Q236H | Q245R | N248S | | |
| V68A | N76D | S103A | V1041 | G159D | A232V | Q236H | Q245R | | |
| V68A | N76D | S103A | V1041 | G159D | P210R | A232V | Q236H | Q245R | |
| V68A | N76D | S103A | V1041 | G159D | A232V | Q236H | Q245R | L257V | |
| N76D | S103A | V1041 | A232V | Q236H | Q245R | L257V | | | |
| V68A | S103A | V1041 | G159D | A232V | Q236H | Q245R | L257V | R275H | |
| N76D | S103A | V1041 | L257V | R275H | | | | | |
| V68A | S103A | V1041 | G1590 | T224A | A232V | Q236H | Q245R | L257V | |
| N76D | S103A | V1041 | G159D | A232V | Q236H | Q245R | L257V | | |
| V68A | N76D | S103A | V1041 | G159D | Y209W | A232V | Q236H | Q245R | |
| V68A | N76D | S103A | V1041 | G159D | G211R | A232V | Q236H | Q245R | |
| V68A | N76D | S103A | V1041 | G159D | G211V | A232V | Q236H | Q245R | |
| Q12R | V68A | N76D | S103A | V1041 | G159D | Y214L | A232V | Q236H | Q245R |
| V68A | N76D | S103A | V1041 | G159D | A215R | A232V | Q236H | Q245R | |
| Q12R | V68A | N76D | S103A | V1041 | G159D | A232V | Q236H | Q245R | |
| G20R | V68A | N76D | S103A | V1041 | G159D | A232V | Q236H | Q245R | S259G |
| V68A | S87R | N76D | S103A | V1041 | G159D | A232V | Q236H | Q245R | T260V |
| V68A | N76D | S103A | V1041 | G159D | A232V | Q236H | Q245R | N261G | |
| V68A | N76D | S103A | V1041 | G159D | A232V | Q236H | Q245R | N261W | |
| N76D | S103A | V1041 | A232V | Q236H | S242P | Q245R | | | |
| V68A | N76D | S103A | V1041 | G159D | P210L | A232V | Q236H | Q245R | |
| Q12R | A48V | V68A | N76D | S103A | V1041 | G159D | A232V | Q236H | Q245R |
| N76D | S103A | V1041 | A232V | Q236H | Q245R | | | | |
| N76D | S103A | V1041 | G159D | Y192F | A232V | Q236H | Q245R | | |
| N76D | S103A | V1041 | V1471 | G159D | A232V | Q236H | Q245R | N248S | K251R |
| Q12R | V68A | N76D | S103A | V1041 | G159D | A232V | Q236H | Q245R | A272S |
| V68A | N76D | S103A | V1041 | G159D | N183K | Q206L | A232V | Q236H | Q245R |
| V68A | N76D | S103A | V1041 | G159D | A232V | Q236H | Q245R | S256R | |

TABLE 2-continued

| | | | | | | | | | | | |
|---|---|---|---|---|---|---|---|---|---|---|---|
| V68A | N76D | S103A | V1041 | G159D | Q206R | A232V | Q236H | Q245R | | | |
| K27R | V68A | N76D | S103A | V1041 | G159D | A232V | Q236H | Q245R | | | |
| V68A | N76D | S103A | V1041 | N116T | G159D | R170S | N185S | A232V | Q236H | Q245R | |
| G61E | V68A | S103A | V1041 | G159D | A232V | Q236H | Q245R | N248D | N252K | | |
| N43D | V68A | S103A | V1041 | G159D | A232V | 0236H | Q245R | N248D | N252K | | |
| V68A | S103A | V1041 | G159D | S212P | A232V | Q236H | Q245R | N248D | N252K | | |
| V68A | S103A | V1041 | S99N | G159D | N184D | A232V | Q236H | Q245R | N248D | N252K | |
| S103A | V1041 | G159D | A232V | Q236H | Q245R | N248D | N252K | | | | |
| V68A | S103A | V1041 | G159D | Y209W | A232V | Q236H | Q245R | N248D | N252K | | |
| V68A | S103A | V1041 | Q109R | G159D | A232V | Q236H | Q245R | N248D | N252K | | |
| G20R | V68A | S103A | V1041 | G159D | A232V | Q236H | Q245R | N248D | N252K | | |
| V68A | S103A | V1041 | G159D | Y209F | A232V | Q236H | Q245R | N248D | N252K | | |
| V68A | S103A | V1041 | G159D | A232V | Q236H | Q245R | N248D | N252K | N261D | | |
| V68A | S103A | V1041 | G1S9D | N185D | A232V | Q236H | Q245R | N248D | N252K | | |
| V68A | S103A | V1041 | G1S9D | P210R | A232V | Q236H | Q245R | N248D | N252K | | |
| V68A | S103A | V1041 | G159D | P210T | A232V | Q236H | Q245R | N248D | N252K | | |
| V68A | S103A | V1041 | G159D | P210S | A232V | Q236H | Q245R | N248D | N252K | | |
| V68A | S103A | V1041 | G159D | N185D | P210L | A232V | Q236H | Q245R | N248D | N252K | |
| V68A | S103A | V1041 | G159D | P210L | A232V | Q236H | Q245R | N248D | N252K | | |
| V68A | S103A | V1041 | G159D | S212A | A232V | Q236H | Q245R | N248D | N252K | | |
| V68A | S103A | V1041 | G159D | S212G | A232V | Q236H | Q245R | N248D | N252K | | |
| V68A | S103A | V1041 | G159D | S212E | A232V | Q236H | Q245R | N248D | N252K | | |
| V68A | S103A | V1041 | G159D | T213E | A232V | Q236H | Q245R | N248D | N252K | | |
| V68A | S103A | V1041 | T213S | A232V | Q236H | Q245R | N248D | N252K | | | |
| V68A | A103V | V1041 | G159D | T213E | A232V | Q236H | Q245R | N248D | N252K | | |
| V68A | S103A | V1041 | G159D | T213R | A232V | Q236H | Q245R | N248D | N252K | | |
| V68A | S103A | V1041 | G159D | T213G | A232V | Q236H | Q245R | N248D | N252K | | |
| V68A | S103A | V1041 | G159D | A215V | A232V | Q236H | Q245R | N248D | N252K | | |
| V68A | S103A | V1041 | G159D | A215R | A232V | Q236H | Q245R | N248D | N252K | | |
| V68A | S103A | V1041 | G159D | S216T | A232V | Q236H | Q245R | N248D | N252K | | |
| V68A | S103A | V1041 | G159D | S216V | A232V | Q236H | Q245R | N248D | N252K | | |
| V68A | S103A | V1041 | G159D | S216C | A232V | Q236H | Q245R | N248D | N252K | | |
| G20A | V68A | S103A | V1041 | G159D | A232V | Q236H | Q245R | N248D | N252K | | |
| V68A | S103A | V1041 | G159D | N173D | A232V | Q236H | Q245R | N248D | N252K | | |
| V68A | S103A | V1041 | G159D | A232V | Q236H | Q245R | N248D | N251V | N252K | | |
| V68A | S103A | V1041 | G159D | Q206R | A232V | Q236H | Q245R | N248D | N252K | | |
| V68A | S103A | V1041 | G159D | A232V | Q236H | Q245R | N248D | N252F | | | |
| V68A | S103A | V1041 | G159D | A232V | Q236H | Q245R | N248D | N252L | | | |
| P55S | V68A | S103A | V1041 | G159D | A232V | Q236H | Q245R | N248D | N252F | | |
| V68A | S103A | V1041 | G159D | A232V | Q236H | Q245R | N248D | N252K | T255V | | |
| V68A | S103A | V1041 | G159D | A232V | Q236H | Q245R | N248D | N252K | S256N | | |
| V68A | S103A | V1041 | G159D | A232V | Q236H | Q245R | N248D | N252K | S256E | | |
| V68A | S103A | V1041 | G159D | A232V | Q236H | Q245R | N248D | N252K | S256R | | |
| V68A | S103A | V1041 | G159D | A232V | Q236H | Q245R | N248D | N252K | T260R | | |
| V68A | S103A | V1041 | G159D | A232V | Q236H | Q245R | N248D | N252K | L257R | | |
| V68A | S103A | V1041 | G159D | A232V | Q236H | Q245R | N248D | N252K | G258D | | |
| I8V | V68A | S103A | V1041 | G159D | A232V | Q236H | Q245R | N248D | N252K | N269D | |
| V68A | S103A | V1041 | N116S | G159D | A232V | Q236H | Q245R | N248D | N252K | N260E | |
| V68A | S103A | V1041 | G159D | A232V | Q236H | Q245R | N248D | N252K | N261D | | |
| V68A | S103A | V1041 | G159D | A232V | Q236H | Q245R | N248D | N252K | N261D | | |
| V68A | N76D | S103A | V1041 | G159D | A232V | Q236H | Q245R | N248D | N252K | | |
| V68A | S103A | V1041 | A232V | Q236H | Q245R | N248D | N252K | | | | |
| S103A | V1041 | G159D | A232S | Q236H | Q245R | N248D | N252K | | | | |
| V68A | S103A | V1041 | G159D | A232V | Q236R | Q245R | N248D | N252K | | | |
| N18S | V68A | S103A | V1041 | G159D | A232V | Q236H | Q245R | N248D | N252K | | |
| V68A | S103A | V1041 | G159D | A232V | Q236H | Q245V | N248D | N252K | | | |
| V68A | N76D | S101T | S103A | V1041 | G159D | T213R | N218S | A232V | Q236H | Q245R | T260A |
| V68A | S103A | V1041 | G159D | A228V | A232V | Q236H | Q245R | N248D | N252K | | |
| T33S | V68A | N76D | S103A | V1041 | G159D | A232V | Q236H | Q245R | N248D | N252K | |
| V68A | N76D | E89D | S103A | V1041 | G159D | P210L | T213R | A232V | Q236H | Q245R | T260A |
| G61E | V68A | N76D | S103A | V1041 | G159D | A232V | Q236H | Q245R | N248D | N252K | |
| S103A | V1041 | G159D | V2051 | P2101 | A232V | Q236H | Q245R | | | | |
| G61E | V68A | S103A | V1041 | S130A | G159D | A232V | Q236H | Q245R | N248D | N252K | |
| G61E | V68A | S103A | V1041 | A133S | Q137R | G159D | A232V | Q236H | Q245R | N248D | N252K |
| G61E | S103A | V1041 | A133V | G159D | A232V | Q236H | Q245R | N248D | N252K | | |
| V68A | S103A | V1041 | G159D | A232V | Q236H | Q245R | N248G | N252K | | | |
| V68A | S103A | V1041 | G159D | N218S | A232V | Q236H | Q245R | N248D | N252K | | |
| G61E | V68A | S103A | V1041 | G159D | S160V | A232V | Q236H | Q245R | N248D | N252K | |
| S3L | G61E | V68A | N76D | S103A | V1041 | A232V | Q236H | Q245R | N248D | N252K | |
| G61E | V68A | S103A | V1041 | G159D | S167F | A232V | Q236H | Q245R | N248D | N252K | |
| G97E | S103A | V1041 | G159D | A232V | Q236H | Q245R | N248D | N252K | | | |
| A98D | S103A | V1041 | G159D | A232V | Q236H | Q245R | N248D | N252K | | | |
| S99E | S103A | V1041 | G159D | A232V | Q236H | Q245R | N248D | N252K | | | |
| S101E | S103A | V1041 | G159D | A232V | Q236H | Q245R | N248D | N252K | | | |
| S101G | S103A | V1041 | G159D | A232V | Q236H | Q245R | N248D | N252K | | | |
| G102A | S103A | V1041 | G159D | A232V | Q236H | Q245R | N248D | N252K | | | |
| S103A | V1041 | S106E | G159D | A232V | Q236H | Q245R | N248D | N252K | | | |
| S103A | V1041 | Q109E | G159D | A232V | Q236H | Q245R | N248D | N252K | | | |
| S103A | V1041 | G159D | A232V | Q236H | Q245R | N248D | N252K | N261R | | | |

TABLE 2-continued

| | | | | | | | | | | | |
|---|---|---|---|---|---|---|---|---|---|---|---|
| S103A | V1041 | Q109R | G159D | A232V | Q236H | Q245R | N248D | N252K | | | |
| N62D | S103A | V1041 | G159D | A232V | Q236H | Q245R | N248D | N252K | | | |
| S103A | V1041 | G159D | N184D | A232V | Q236H | Q245R | N248D | N252K | | | |
| S103A | V1041 | G159D | S166D | A232V | Q236H | Q245R | N248D | N252K | | | |
| S103A | V1041 | G159D | L217E | A232V | Q236H | Q245R | N248D | N252K | | | |
| G20R | N62D | S103A | V1041 | G159D | T213R | A232V | Q236H | Q245R | N248D | N252K | |
| N62D | S103A | V1041 | G159D | T213R | A232V | Q236H | 0245R | N248D | N252K | | |
| S103A | V1041 | G159D | Q206R | L217E | A232V | Q236H | Q245R | N248D | N252K | | |
| N62D | S103A | V1041 | G159D | Q206R | A232V | Q236H | Q245R | N248D | N252K | | |
| S103A | V1041 | S130G | G159D | A232V | Q236H | Q245R | N248D | N252K | | | |
| S103A | V1041 | P131V | G159D | A232V | Q236H | Q245R | N248D | N252K | | | |
| K27N | S103A | V1041 | G159D | A232V | Q236H | Q245R | N248D | N252K | | | |
| T38G | S103A | V1041 | G159D | A232V | Q236H | Q245R | N248D | N252K | | | |
| T38A | N76D | S103A | V1041 | G159D | T213R | A232V | Q236H | Q245R | T260A | | |
| V68A | N76D | S103A | V1041 | G159D | T213R | A232V | Q236H | Q245R | T260A | E271G | |
| V68A | N76D | S103A | V1041 | G159D | Y209W | T213R | A232V | Q236H | Q245R | T260A | |
| V68A | N76D | S103A | V1041 | G159D | P2101 | T213R | A232V | Q236H | Q245R | T260A | |
| V68A | N76D | S103A | V1041 | G159D | V2051 | T213R | A232V | Q236H | Q245R | T260A | |
| V68A | N76D | S103A | V1041 | G159D | P2101 | A232V | Q236H | Q245R | T260A | | |
| V68A | S103A | V1041 | G159D | T213R | A232V | Q236H | Q245R | T260A | | | |
| N76D | S103A | V1041 | G159D | T213R | A232V | Q236H | Q245R | T260A | | | |
| V68A | S103A | V1041 | G159D | Y209W | A232V | Q236H | Q245R | | | | |
| V68A | S103A | V1041 | G159D | P2101 | A232V | Q236H | Q245R | | | | |
| V68A | S103A | V1041 | G159D | A230V | A232V | Q236H | Q245R | | | | |
| V68A | S103A | V1041 | G159D | L126F | A232V | Q236H | Q245R | | | | |
| V68A | S103A | V1041 | G159D | V2051 | A232V | Q236H | Q245R | | | | |
| V68A | S103A | V1041 | G159D | P210L | A232V | Q236H | Q245R | | | | |
| S103A | V1041 | G159D | A230V | Q236H | Q245R | | | | | | |
| V68A | S103A | V1041 | G159D | A232V | Q236H | Q245R | T260A | | | | |
| S103A | V1041 | G159D | A232V | Q236H | Q245R | | | | | | |
| V68A | S103A | V1041 | G159D | A174V | A232V | Q236H | Q245R | L257V | | | |
| V68A | S103A | V1041 | G159D | A194S | A232V | Q236H | Q245R | L257V | | | |
| V68A | S103A | V1041 | G159D | Y209W | A232V | Q236H | Q245R | L257V | | | |
| S103A | V1041 | G159D | A232V | Q236H | Q245R | L257V | | | | | |
| V68A | N76D | S103A | V1041 | G159D | T213R | A232V | Q236H | Q245R | T260A | N261W | |
| V68A | S103A | V1041 | G159D | A232V | Q236H | Q245R | L257V | N261W | | | |
| S103A | V1041 | G159D | T213R | A232V | Q236H | Q245R | T260A | | | | |
| S103A | V1041 | G159D | P2101 | A232V | Q236H | Q245R | N248D | N252K | | | |
| S103A | V1041 | G159D | Y209W | A232V | Q236H | Q245R | L257V | | | | |
| V68A | N76D | S103A | V1041 | G159D | P210L | T213R | A232V | Q236H | Q245R | T260A | |
| Q12R | S103A | V1041 | G159D | Y209W | T213R | A232V | Q236H | Q245R | T260A | | |
| S103A | V1041 | Y209W | A232V | Q236H | Q245R | L257V | | | | | |
| S103A | V1041 | G159D | V2051 | P2101 | T213R | A232V | Q236H | Q245R | T260A | | |
| S103A | V1041 | G159D | V2051 | Y209W | A232V | Q236H | Q245R | T260A | | | |
| V68A | S103A | V1041 | G159D | V2051 | Y209W | P2101 | A232V | Q236H | Q245R | | |
| S103A | V1041 | G159D | V2051 | Y209W | P2101 | A232V | Q236H | Q245R | L257V | | |
| S103A | V1041 | G159D | V2051 | Y209W | A232V | Q236H | Q245R | L257V | | | |
| V68A | S103A | V1041 | G159D | V2051 | Y209W | P2101 | A232V | Q236H | Q245R | T260A | |
| S103A | V1041 | G159D | V2051 | Y209W | P2101 | A232V | Q236H | Q245R | | | |
| S103A | V1041 | G159D | Y209W | P2101 | A232V | Q236H | Q245R | | | | |
| S103A | V1041 | G159D | V2051 | P2101 | A232V | Q236H | Q245R | | | | |
| V68A | S103A | V1041 | S128L | G159D | A232V | Q236H | Q245R | | | | |
| A48V | S103A | V1041 | G159D | A230V | Q236H | Q245R | | | | | |
| A48V | V68A | S103A | V1041 | G159D | Y209W | A232V | Q236H | Q245R | | | |
| A48V | V68A | S103A | V1041 | G159D | A232V | Q236H | Q245R | N248D | N252K | | |
| A48V | V68A | S103A | V1041 | G159D | A232V | Q236H | Q245R | L257V | N261W | | |
| G102A | S103A | V1041 | G159D | S212G | A232V | Q236H | Q245R | N248D | N252K | | |
| Q12R | G102A | S103A | V1041 | G159D | S212G | A232V | Q236H | Q245R | N248D | N252K | |
| S101G | G102A | S103A | V1041 | G159D | S212G | A232V | Q236H | Q245R | N248D | N252K | |
| A98L | G102A | S103A | V1041 | G159D | S212G | A232V | Q236H | Q245R | N248D | N252K | |
| G102A | S103A | V1041 | G159D | T213R | A232V | Q236H | Q245R | N248D | N252K | | |
| S103A | V1041 | P131V | G159D | A232V | Q236H | Q245R | N248D | N252K | | | |
| S103A | V1041 | G159D | N184S | A232V | Q236H | Q245R | N248D | N252K | | | |
| S103A | V1041 | G159D | N184G | A232V | Q236H | Q245R | N248D | N252K | | | |
| S103A | V1041 | G159D | A232V | Q236H | V244T | Q245R | N248D | N252K | | | |
| S103A | V1041 | G159D | A232V | Q236H | V244A | Q245R | N248D | N252K | | | |
| N62D | S103A | V1041 | G159D | T213R | A232V | Q236H | Q245R | N248D | N252K | S256R | |
| Q12R | N62D | S103A | V1041 | G159D | T213R | A232V | Q236H | Q245R | N248D | N252K | |
| S101G | S103A | V1041 | G159D | N185D | A232V | Q236H | Q245R | N248D | N252K | | |
| S101G | S103A | V1041 | G159D | Q206E | A232V | Q236H | Q245R | N248D | N252K | | |
| S101G | S103A | V1041 | G159D | T213Q | A232V | Q236H | Q245R | N248D | N252K | | |
| A98L | G102A | S103A | V1041 | G159D | A232V | Q236H | Q245R | N248D | N252K | | |
| S101G | G102A | S103A | V1041 | G159D | A232V | Q236H | Q245R | N248D | N252K | | |
| A98L | G102A | S103A | V1041 | G159D | S212G | A232V | Q236H | Q245R | N248D | N252K | |
| A98L | G102A | S103A | V1041 | G159D | S212G | A232V | Q236H | N248D | N252K | | |
| N62D | S103A | V1041 | Q109R | G159D | T213R | A232V | Q236H | Q245R | N248D | N252K | |
| N62D | S103A | V1041 | G159D | S212G | T213R | A232V | Q236H | Q245R | N248D | N252K | |
| N62D | S101G | S103A | V1041 | G159D | S212G | T213R | A232V | Q236H | Q245R | N248D | N252K |
| S103A | V1041 | G159D | A232V | Q245R | N248D | N252K | | | | | |

TABLE 2-continued

| | | | | | | | | | | | | |
|---|---|---|---|---|---|---|---|---|---|---|---|---|
| S103A | V1041 | G159D | A230V | Q245R | | | | | | | | |
| N62D | S103A | V1041 | S130G | G159D | T213R | A232V | Q236H | Q245R | N248D | N252K | | |
| S101G | S103A | V1041 | S130G | G159D | A232V | Q236H | Q245R | N248D | N252K | | | |
| S101G | S103A | V1041 | S128G | G159D | A232V | Q236H | Q245R | N248D | N252K | | | |
| S101G | S103A | V1041 | S128L | G159D | A232V | Q236H | Q245R | N248D | N252K | | | |
| N62D | S101G | S103A | V1041 | G159D | T213R | A232V | Q236H | Q245R | N248D | N252K | | |
| N62D | S103A | V1041 | S128G | G159D | T213R | A232V | Q236H | Q245R | N248D | N252K | | |
| N62D | S103A | V1041 | S128L | G159D | T213R | A232V | Q236H | Q245R | N248D | N252K | | |
| S101G | S103A | V1041 | G159D | A232V | Q236H | Q245R | N248D | N252K | T260A | | | |
| S101G | S103A | V1041 | P131V | G159D | A232V | Q236H | Q245R | N248D | N252K | | | |
| A98V | S101G | S103A | V1041 | G159D | A232V | Q236H | Q245R | N248D | N252K | | | |
| S99G | S101G | S103A | V1041 | G159D | A232V | Q236H | Q245R | N248D | N252K | | | |
| S101G | S103A | V1041 | G159D | S212G | A232V | Q236H | Q245R | N248D | N252K | | | |
| S101G | S103A | V1041 | G159D | Y209W | A232V | Q236H | Q245R | N248D | N252K | | | |
| S101G | S103A | V1041 | G159D | P2101 | A232V | Q236H | Q245R | N248D | N252K | | | |
| S101G | S103A | V1041 | G159D | V2051 | A232V | Q236H | Q245R | N248D | N252K | | | |
| S101G | S103A | V1041 | G159D | A230V | Q236H | Q245R | | | | | | |
| S101G | S103A | V1041 | G159D | A194P | A232V | Q236H | Q245R | N248D | N252K | | | |
| N76D | S101G | S103A | V1041 | G159D | A194P | A232V | Q236H | Q245R | N248D | N252K | | |
| S101G | S103A | V1041 | G159D | A230V | A232V | Q236H | Q245R | N248D | N252K | | | |
| N62D | S103A | V1041 | G159D | N185D | Q206E | T213R | A232V | Q236H | Q245R | N248D | N252K | E271Q |

It is a further object to provide DNA sequences encoding such protease variants, as well as expression vectors containing such variant DNA sequences.

Still further, another object of the invention is to provide host cells transformed with such vectors, as well as host cells which are capable of expressing such DNA to produce protease variants either intracellularly or extracellularly.

There is further provided a cleaning composition comprising a protease variant of the present invention.

Additionally, there is provided an animal feed comprising a protease variant of the present invention.

Also provided is a composition for the treatment of a textile comprising a protease variant of the present invention.

BRIEF DESCRIPTION OF THE DRAWINGS

FIGS. 1 A–B depict the DNA (SEQ ID NO:1) and amino acid sequence (SEQ ID NO:2) for *Bacillus amyloliquefaciens* subtilisin and a partial restriction map of this gene.

FIG. 2 depicts the conserved amino acid residues among subtilisins from *Bacillus amyloliquefaciens* (BPN)' and *Bacillus lentus* (wild-type).

FIGS. 3A and 3B depict the amino acid sequence of four subtilisins. The top line represents the amino acid sequence of subtilisin from *Bacillus amyloliquefaciens* subtilisin (also sometimes referred to as subtilisis-BPN')(SEQ ID NO:5). The second line depicts the amino acid sequence of subtilisin from *Bacillus subtilis* (SEQ ID NO:4). The third line depicts the amino acid sequence of subtilisin from *B. licheniformis* (SEQ ID NO:5). The fourth line depicts the amino acid sequence of subtilisin from *Bacillus lentus* (also referred to as subtilisin 309 in PCT WO89/06276)(SEQ ID NO:6). The symbol denotes the absence of specific amino acid residues as compared to subtilisin BPN'.

DETAILED DESCRIPTION OF THE INVENTION

Proteases are carbonyl hydrolases which generally act to cleave peptide bonds of proteins or peptides. As used herein, "protease" means a naturally-occurring protease or a recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

The present invention includes protease enzymes which are non-naturally occurring carbonyl hydrolase variants (protease variants) having a different proteolytic activity, stability, substrate specificity, pH profile and/or performance characteristic as compared to the precursor carbonyl hydrolase from which the amino acid sequence of the variant is derived. Specifically, such protease variants have an amino acid sequence not found in nature, which is derived by substitution of a plurality of amino acid residues of a precursor protease with different amino acids. The precursor protease may be a naturally-occurring protease or a recombinant protease.

The protease variants useful herein encompass the substitution of any of the nineteen naturally occurring L-amino acids at the designated amino acid residue positions. Such substitutions can be made in any precursor subtilisin (procaryotic, *eucaryotic, mammalian, etc.). Throughout this application reference is made to various amino acids by way of common one—and three-letter codes. Such codes are identified in Dale, M. W. (1989), *Molecular Genetics of Bacteria*, John Wiley & Sons, Ltd., Appendix B.

The protease variants useful herein are preferably derived from a Bacillus .subtilisin. More preferably, the protease variants are derived from *Bacillus lentus* subtilisin and/or subtilisin 309.

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartateserine. Thus, subtilisin herein refers to a serine protease having the catalytic triad of subtilisin related proteases. Examples include but are not limited to the subtilisins identified in FIG. 3 herein. Generally and for purposes of the present invention, numbering of the amino acids in proteases corresponds to the numbers assigned to the mature *Bacillus amyloliquefaciens* subtilisin sequence presented in FIG. 1.

"Recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. RE. No. 34,606, U.S. Pat. No. 5,204,015 and U.S. Pat. No. 5,185,258, U.S. Pat. No. 5,700,676, U.S. Pat. No. 5,801,038, and U.S. Pat. No. 5,763,257.

"Non-human subtilisins" and the DNA encoding them may be obtained from many procaryotic and eucaryotic organisms. Suitable examples of procaryotic organisms include gram negative organisms such as *E. coli* or Pseudomonas and gram positive bacteria such as *Micrococcus or Bacillus*. Examples of eucaryotic organisms from which subtilisin and their genes may be obtained include yeast such as *Saccharomyces cerevisiae*, fungi such as Aspergillus sp.

A "protease variant" has an amino acid sequence which is derived from the amino acid sequence of a "precursor protease". The precursor proteases include naturally-occurring proteases and recombinant proteases. The amino acid sequence of the protease variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods known to those skilled in the art (see, for example, EP 0 328299, WO89/06279 and the US patents and applications already referenced herein).

Specific substitutions of amino acids at one or more residue positions corresponding to residue positions selected from the group consisting of 62, 212, 230, 232, 252 and 257 of *Bacillus amyloliquefaciens* subtilisin are identified herein.

Preferred variants are those having combinations of substitutions at residue positions corresponding to positions of *Bacillus amyloliquefaciens* subtilisin in Table 1.

More preferred variants are those having combinations of substitutions at residue positions corresponding to positions of *Bacillus amyloliquefaciens* subtilisin in Table 2.

Further preferred variants are those having combinations of substitutions at residue positions corresponding to positions of *Bacillus amyloliquefaciens* subtilisin in Table 3.

TABLE 3

| | | | | | | | | | |
|---|---|---|---|---|---|---|---|---|---|
| 68 | 103 | 104 | 159 | 232 | 236 | 245 | 252 | | |
| 68 | 76 | 103 | 104 | 159 | 213 | 232 | 236 | 245 | 260 |
| 68 | 103 | 104 | 159 | 232 | 236 | 245 | 248 | 252 | |
| 68 | 103 | 104 | 159 | 232 | 236 | 245 | | | |
| 68 | 103 | 104 | 140 | 159 | 232 | 236 | 245 | 252 | |
| 43 | 68 | 103 | 104 | 159 | 232 | 236 | 245 | 252 | |
| 43 | 68 | 103 | 104 | 159 | 232 | 236 | 245 | | |
| 68 | 103 | 104 | 159 | 232 | 236 | 245 | 257 | | |
| 68 | 76 | 103 | 104 | 159 | 210 | 232 | 236 | 245 | |
| 68 | 103 | 104 | 159 | 224 | 232 | 236 | 245 | 257 | |
| 76 | 103 | 104 | 159 | 232 | 236 | 245 | 257 | | |
| 68 | 76 | 103 | 104 | 159 | 211 | 232 | 236 | 245 | |
| 12 | 68 | 76 | 103 | 104 | 159 | 214 | 232 | 236 | 245 |
| 68 | 76 | 103 | 104 | 159 | 215 | 232 | 236 | 245 | |
| 12 | 68 | 76 | 103 | 104 | 159 | 232 | 236 | 245 | |
| 20 | 68 | 76 | 103 | 104 | 159 | 232 | 236 | 245 | 259 |
| 68 | 76 | 87 | 103 | 104 | 159 | 232 | 236 | 245 | 260 |
| 68 | 76 | 103 | 104 | 159 | 232 | 236 | 245 | 261 | |
| 12 | 48 | 68 | 76 | 103 | 104 | 159 | 232 | 236 | 245 |
| 76 | 103 | 104 | 159 | 192 | 232 | 236 | 245 | | |
| 76 | 103 | 104 | 147 | 159 | 232 | 236 | 245 | 248 | 251 |
| 12 | 68 | 76 | 103 | 104 | 159 | 232 | 236 | 245 | 272 |
| 68 | 76 | 103 | 104 | 159 | 183 | 206 | 232 | 236 | 245 |
| 68 | 76 | 103 | 104 | 159 | 232 | 236 | 245 | 256 | |
| 68 | 76 | 103 | 104 | 159 | 206 | 232 | 236 | 245 | |
| 27 | 68 | 76 | 103 | 104 | 159 | 232 | 236 | 245 | |
| 68 | 103 | 104 | 159 | 212 | 232 | 236 | 245 | 248 | 252 |
| 103 | 104 | 159 | 232 | 236 | 245 | 248 | 252 | | |
| 68 | 103 | 104 | 159 | 209 | 232 | 236 | 245 | 248 | 252 |
| 68 | 103 | 104 | 109 | 159 | 232 | 236 | 245 | 248 | 252 |
| 20 | 68 | 103 | 104 | 159 | 232 | 236 | 245 | 248 | 252 |
| 68 | 103 | 104 | 159 | 209 | 232 | 236 | 245 | 248 | 252 |
| 68 | 103 | 104 | 159 | 210 | 232 | 236 | 245 | 248 | 252 |
| 68 | 103 | 104 | 159 | 212 | 232 | 236 | 245 | 248 | 252 |
| 68 | 103 | 104 | 159 | 213 | 232 | 236 | 245 | 248 | 252 |
| 68 | 103 | 104 | 213 | 232 | 236 | 245 | 248 | 252 | |
| 68 | 103 | 104 | 159 | 215 | 232 | 236 | 245 | 248 | 252 |
| 68 | 103 | 104 | 159 | 216 | 232 | 236 | 245 | 248 | 252 |
| 20 | 68 | 103 | 104 | 159 | 232 | 236 | 245 | 248 | 252 |
| 68 | 103 | 104 | 159 | 232 | 236 | 245 | 248 | 252 | 255 |
| 68 | 103 | 104 | 159 | 232 | 236 | 245 | 248 | 252 | 256 |

TABLE 3-continued

| | | | | | | | | | | | |
|---|---|---|---|---|---|---|---|---|---|---|---|
| 68 | 103 | 104 | 159 | 232 | 236 | 245 | 248 | 252 | 260 | | |
| 68 | 103 | 104 | 159 | 228 | 232 | 236 | 245 | 248 | 252 | | |
| 68 | 76 | 89 | 103 | 104 | 159 | 210 | 213 | 232 | 236 | 245 | 260 |
| 68 | 103 | 104 | 159 | 218 | 232 | 236 | 245 | 248 | 252 | | |

These amino acid position numbers refer to those assigned to the mature *Bacillus amyloliquefaciens* subtilisin sequence presented in FIG. 1. The invention, however, is not limited to the mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is *Bacillus lentus* subtilisin and the substitutions are made at the equivalent amino acid residue positions in *B. lentus* corresponding to those listed above.

A residue (amino acid) position of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor protease is directly compared to the *Bacillus amyloliquefaciens* subtilisin primary sequence and particularly to a set of residues known to be invariant in subtilisins for which sequence is known. For example, FIG. 2 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained. Siezen et al. (1991) *Protein Eng.* 4(7):719–737 shows the alignment of a large number of serine proteases. Siezen et al. refer to the grouping as subtilases or subtilisin-like serine proteases.

For example, in FIG. 3, the amino acid sequence of subtilisin from *Bacillus amyloliquefaciens, Bacillus subtilis, Bacillus licheniformis* (carlsbergensis) and *Bacillus lentus* are aligned to provide the maximum amount of homology between amino acid sequences. A comparison of these sequences shows that there are a number of conserved residues contained in each sequence. These conserved residues (as between BPN' and *B. lentus*) are identified in FIG. 2.

These conserved residues, thus, may be used to define the corresponding equivalent amino acid residues of *Bacillus amyloliquefaciens* subtilisin in other subtilisins such as subtilisin from *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val 65 in *Bacillus amyloliquefaciens* subtilisin in the other subtilisins is isoleucine for *B. lentus* and *B. licheniformis.*

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protease in question to the *Bacillus amyloliquefaciens* subtilisin. The best model is the crystallographic model giving the lowest R factor for experimental diffraction data at the highest resolution available.

$$R\ factor = \frac{\sum_h |Fo(h)| - |Fc(h)|}{\sum_h |Fo(h)|}$$

Equivalent residues which are functionally analogous to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution are conserved residues whereas others are not. In the case of residues which are not conserved, the substitution of one or more amino acids is limited to substitutions which produce a variant which has an amino acid sequence that does not correspond to one found in nature. In the case of conserved residues, such substitutions should not result in a naturally-occurring sequence. The protease variants of the present invention include the mature forms of protease variants, as well as the pro- and prepro-forms of such protease variants. The prepro-forms are the preferred construction since this facilitates the expression, secretion and maturation of the protease variants.

"Prosequence" refers to a sequence of amino acids bound to the N-terminal portion of the mature form of a protease which when removed results in the appearance of the "mature" form of the protease. Many proteolytic enzymes are found in nature as translational proenzyme products and, in the absence of post-translational processing, are expressed in this fashion. A preferred prosequence for producing protease variants is the putative prosequence of *Bacillus amyloliquefaciens* subtilisin, although other protease prosequences may be used.

A "signal sequence" or "presequence" refers to any sequence of amino acids bound to the N-terminal portion of a protease or to the N-terminal portion of a proprotease which may participate in the secretion of the mature or pro forms of the protease. This definition of signal sequence is a functional one, meant to include all those amino acid sequences encoded by the N-terminal portion of the protease gene which participate in the effectuation of the secretion of protease under native conditions. The present invention utilizes such sequences to effect the secretion of the protease variants as defined herein. One possible signal sequence comprises the first seven amino acid residues of the signal sequence from *Bacillus subtilis* subtilisin fused to the remainder of the signal sequence of the subtilisin from *Bacillus lentus* (ATCC 21536).

A "prepro" form of a protease variant consists of the mature form of the protease having a prosequence operably linked to the amino terminus of the protease and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. RE. No. 34,606 to render them incapable of secreting enzymatically active endoprotease. A preferred host cell for expressing protease is the Bacillus strain BG2036 which is deficient in enzymatically active neutral protease and alkaline protease (subtilisin). The construction of strain BG2036 is described in detail in U.S. Pat. No. 5,264,366. Other host cells for expressing protease include *Bacillus subtilis* I168 (also described in U.S. Pat. RE. No. 34,606 and U.S. Pat. No. 5,264,366, the disclosure of which are incorporated herein by reference), as well as any suitable Bacillus strain such as *B. licheniformis, B. lentus*, etc.

Host cells are transformed or transfected with vectors constructed using recombinant DNA techniques. Such transformed host cells are capable of either replicating vectors encoding the protease variants or expressing the desired protease variant. In the case of vectors which encode the pre- or prepro-form of the protease variant, such variants, when expressed, are typically secreted from the host cell into the host cell medium.

"Operably linked, " when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protease may be obtained in accord with the general methods known to those skilled in the art. The methods generally comprise synthesizing labeled probes having putative sequences encoding regions of the protease of interest, preparing genomic libraries from organisms expressing the protease, and screening the libraries for the gene of interest by hybridization to the probes. Positively hybridizing clones are then mapped and sequenced.

The cloned protease is then used to transform a host cell in order to express the protease. The protease gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the protease gene in certain eucaryotic host cells) which is exogenous or is supplied by the endogenous terminator region of the protease gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the protease gene into host genome. This is facilitated by procaryotic and eucaryotic organisms which are particularly susceptible to homologous recombination.

The gene can be a natural *B. lentus* gene. Alternatively, a synthetic gene encoding a naturally-occurring or mutant precursor protease may be produced. in such an approach, the DNA and/or amino acid sequence of the precursor protease is determined. Multiple, overlapping synthetic single-stranded DNA fragments are thereafter synthesized, which upon hybridization and ligation produce a synthetic DNA encoding the precursor protease. An example of synthetic gene construction is set forth in Example 3 of U.S. Pat. No. 5,204,015, the disclosure of which is incorporated herein by reference.

Once the naturally-occurring or synthetic precursor protease gene has been cloned, a number of modifications are undertaken to enhance the use of the gene beyond synthesis of the naturally-occurring precursor protease. Such modifications include the production of recombinant proteases as disclosed in U.S. Pat. RE. No. 34,606 and EPO Publication No. 0 251 446 and the production of protease variants described herein.

The following cassette mutagenesis method may be used to facilitate the construction of the protease variants of the present invention, although other methods may be used. First, the naturally-occurring gene encoding the protease is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protease gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction.

Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, proteolytic activity is defined as the rate of hydrolysis of peptide bonds per milligram of active enzyme. Many well known procedures exist for measuring proteolytic activity (K. M. Kalisz, "Microbial Proteinases," *Advances in Biochemical Engineering/Biotechnology*, A. Fiechter ed., 1988). In addition to or as an alternative to modified proteolytic activity, the variant enzymes of the present invention may have other modified properties such as $K_m$, $k_{cat}$, $k_{cat}/K_m$ ratio and/or modified substrate specificity and/or modified pH activity profile. These enzymes can be tailored for the particular substrate which is anticipated to be present, for example, in the preparation of peptides or for hydrolytic processes such as laundry uses.

In one aspect of the invention, the objective is to secure a variant protease having altered, preferably improved wash performance as compared to a precursor protease in at least one detergent formulation and or under at least one set of wash conditions.

There is a variety of wash conditions including varying detergent formulations, wash water volume, wash water temperature and length of wash time that a protease variant might be exposed to. For example, detergent formulations used in different areas have different concentrations of their relevant components present in the wash water. For example, a European detergent typically has about 4500–5000 ppm of detergent components in the wash water while a Japanese detergent typically has approximately 667 ppm of detergent components in the wash water. In North America, particularly the United States, a detergent typically has about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500–5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe.

Accordingly one aspect of the present invention includes a protease variant that shows improved wash performance in at least one set of wash conditions.

In another aspect of the invention, it has been determined that substitution of an amino acid at one or more residue positions corresponding to residue positions selected from the group consisting of 62, 212, 230, 232, 252 and 257 of *Bacillus amyloliquefaciens* subtilisin are important in improving the wash performance of the enzyme.

These substitutions are preferably made in *Bacillus lentus* (recombinant or native-type) subtilisin, although the substitutions may be made in any Bacillus protease.

Based on the screening results obtained with the variant proteases, the noted mutations in *Bacillus amyloliquefaciens* subtilisin are important to the proteolytic activity, performance and/or stability of these enzymes and the cleaning or wash performance of such variant enzymes.

Many of the protease variants of the invention are useful in formulating various detergent compositions or personal care formulations such as shampoos or lotions. A number of known compounds are suitable surfactants useful in compositions comprising the protease mutants of the invention. These include nonionic, anionic, cationic, or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protease variants of the present invention may be used for any purpose that native or wild-type proteases are used. Thus, these variants can be used, for example, in bar or liquid soap applications, dishcare formulations, contact lens cleaning solutions or products, peptide hydrolysis, waste treatment, textile applications, as fusion-cleavage enzymes in protein production, etc. The variants of the present invention may comprise enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteases of the invention to conventional cleaning compositions does not create any special use limitation. In other words, any temperature and pH suitable for the detergent is also suitable for the present compositions as long as the pH is within the above range, and the temperature is below the described protease's denaturing temperature. In addition, proteases of the invention can be used in a cleaning composition without detergents, again either alone or in combination with builders and stabilizers.

The present invention also relates to cleaning compositions containing the protease variants of the invention. The cleaning compositions may additionally contain additives which are commonly used in cleaning compositions. These can be selected from, but not limited to, bleaches, surfactants, builders, enzymes and bleach catalysts. It would be readily apparent to one of ordinary skill in the art what additives are suitable for inclusion into the compositions. The list provided herein is by no means exhaustive and should be only taken as examples of suitable additives. It will also be readily apparent to one of ordinary skill in the art to only use those additives which are compatible with the enzymes and other components in the composition, for example, surfactant.

When present, the amount of additive present in the cleaning composition is from about 0.01% to about 99.9%, preferably about 1% to about 95%, more preferably about 1% to about 80%.

The variant proteases of the present invention can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes variant proteases of the present invention. The composition can be used to treat for example silk or wool as described in publications such as RD 216,034; EP 134,267; U.S. Pat. No. 4,533,359; and EP 344,259.

The following is presented by way of example and is not to be construed as a limitation to the scope of the claims.

All publications and patents referenced herein are hereby incorporated by reference in their entirety.

EXAMPLE 1

A large number of protease variants were produced and purified using methods well known in the art. All mutations were made in *Bacillus lentus* GG36 subtilisin. The variants are shown in Table 4.

TABLE 4

| | | | | |
|---|---|---|---|---|
| N76D | S103A | V104I | M222S | |
| N76D | A98E | S103A | V104I | |
| N76D | S78T | S103A | V104I | |
| N76D | S103A | V104I | I107V | |
| V4E | N76D | S103A | V104I | |
| N76D | S103A | V104I | I246V | |
| N76D | N77D | S103A | V104I | |
| N76D | S103A | V104I | N183D | N2181 |
| A16T | N76D | S103A | V104I | N248D |
| A1E | N76D | S103A | V104I | |
| N76D | S103A | V104I | N261D | |
| N76D | S103A | V104I | S160T | |
| N76D | S103A | V104I | S216C | |
| HA7Q | N76D | S103A | V104I | |

TABLE 4-continued

| | | | | | | |
|---|---|---|---|---|---|---|
| S37T | N76D | S103A | V104I | | | |
| N76D | N77D | S103A | V104I | A174V | | |
| T38S | N76D | S103A | V104I | | | |
| T38S | N76D | S103A | V104I | K237Q | | |
| I8V | N76D | S1O3A | V104I | | | |
| N76D | S103A | V104I | N183D | | | |
| R19L | N76D | S103A | V104I | | | |
| A13V | N76D | S103A | V104I | | | |
| R19C | N76D | S103A | V104I | | | |
| N76D | S103A | V104I | N184D | | | |
| N76D | S103A | V104I | N252D | | | |
| N76D | S103A | V104I | S259C | | | |
| N76D | S103A | V104I | K251T | | | |
| N76D | P86S | S103A | V104I | | | |
| I72V | N76D | S103A | V104I | N185D | | |
| N76D | S103A | V104I | K237E | T274A | | |
| N76D | S103A | V104I | S160L | | | |
| N76D | S103A | V104I | A228V | | | |
| P55S | N76D | S103A | V104I | S240T | | |
| N76D | S103A | V104I | A254T | | | |
| N76D | S103A | I104N | N204T | | | |
| N76D | S103A | V104I | N204D | | | |
| N43S | N76D | S103A | V104I | | | |
| N76D | S103A | V104I | G159D | | | |
| R10H | N76D | S103A | V104I | V177A | | |
| T58S | N76D | S103A | V104I | | | |
| N76D | S103A | V104I | A270V | | | |
| N76D | S103A | V104I | N185D | | | |
| K27N | N76D | S103A | V104I | | | |
| N76D | S103A | V104I | L262M | | | |
| N76D | S78P | S103A | V104I | | | |
| S24P | N76D | S103A | V104I | | | |
| N76D | S103A | V104I | S166G | Q236R | K251R | |
| H17L | N76D | S103A | V104I | K237E | | |
| N76D | S103A | V104I | S130L | | | |
| N76D | S103A | V104I | Q109R | | | |
| N76D | S99R | S103A | V104I | N204T | | |
| N76D | S103A | V104I | D181N | | | |
| Q12R | N76D | S103A | V104I | | | |
| N76D | S103A | V104I | S212P | E271V | | |
| N76D | S103A | V104I | N252k | N261Y | | |
| N76D | S103A | V104I | S242T | | | |
| N76D | S103A | V104I | E271Q | | | |
| Q12R | N76D | S103A | V104I | S242T | | |
| N43S | N76D | S103A | V104I | N116K | N183I | |
| N76D | S103A | V104I | G258R | | | |
| N76D | S103A | V104I | E271G | | | |
| G61R | N76D | S103A | V104I | | | |
| T38S | N76D | S103A | V104I | Q182R | Y263H | |
| N76D | S103A | V104I | Q182R | A272S | | |
| N76D | S103A | V104I | Q109R | I246V | | |
| N76D | S87G | S103A | V104I | Q206R | H249Q | S265G |
| N76D | S103A | V104I | Q137R | N238Y | E271V | |
| S103A | V104I | A228T | | | | |
| N76D | S103A | V104I | Q182R | I198V | | |
| L21M | N76D | S103A | V104I | Q182R | | |
| N76D | S103A | V104I | M119I | Q137R | | |
| N76D | S103A | V104I | Q137R | N2485 | | |
| A13T | N76D | S103A | V104I | Q206R | | |
| N76D | S103A | V104I | Q206R | | | |
| N76D | S103A | V104I | S212P | G258R | | |
| T58S | N76D | S103A | V104I | E271G | | |
| N76D | S103A | V104I | Q206E | N261D | | |
| V4E | N76D | S103A | V104I | Q206E | | |
| N76D | N77D | S103A | V104I | Q206E | | |
| N76D | S103A | V104I | A158E | | | |
| N76D | S103A | V104I | Q206E | | | |
| V4E | N76D | S103A | V104I | G159D | L217E | K251Q |
| V4E | N76D | S103A | V104I | G159D | L217E | N252D |
| N76D | N77D | S103A | V104I | A133T | N185D | K251T |
| N76D | S103A | V104I | G159D | Q206E | V244A | |
| V4E | N76D | S103A | V104I | S188E | | |
| V4E | N76D | S103A | V104I | A158E | | |
| N76D | N77D | S103A | V104I | N185D | | |
| N76D | S103A | V104I | Q206E | K251T | | |
| A48T | N76D | S103A | V104I | L111M | G159D | |
| V68A | N76D | S103A | V104I | G159D | Q236H | |
| L42V | N76D | S103A | V104I | G159D | | |
| Q12H | N62H | N76D | S103A | V104I | G159D | |

TABLE 4-continued

| | | | | | | | | | |
|---|---|---|---|---|---|---|---|---|---|
| L42I | N76D | S103A | V104I | G159D | | | | | |
| N76D | S103A | V104I | G146S | G159D | | | | | |
| N76D | S103A | V104I | G159D | N238S | | | | | |
| N76D | S103A | V104I | G1S9D | T224A | | | | | |
| N76D | S103A | V104I | S212P | V268F | E271V | | | | |
| N76D | E89A | S103A | V104I | | | | | | |
| N76D | S87R | S103A | V104I | S212P | E271V | | | | |
| N76D | S103A | V104I | 5212P | Q245L | E271V | | | | |
| N76D | S103A | V104I | T134S | S141N | 5212P | E271V | | | |
| N76D | S103A | V104I | S212P | Q236L | N243S | E271V | | | |
| N76D | S103A | V104I | Q109R | Q245R | | | | | |
| N76D | S103A | V104I | Q109R | P210L | | | | | |
| G20V | N62S | N76D | S103A | V104I | | | | | |
| V68A | N76D | S103A | V104I | Q236H | | | | | |
| V68A | N76D | S103A | V104I | G159D | Q236H | E271V | | | |
| V68A | N76D | S103A | V104I | G159D | Q236H | Q245R | | | |
| V68A | N76D | S103A | V104I | G159D | L217I | Q236H | E271V | | |
| H17Q | V68A | N76D | S103A | V104I | | | | | |
| V68A | N76D | S103A | V104I | | | | | | |
| V68A | N76D | S103A | V104I | G159D | Q236R | | | | |
| V68A | L75R | N76D | S103A | V104I | G159D | Q236H | | | |
| V68A | N76D | N76D | S103A | A114V | V121I | G159D | Q236H | Q245R | |
| Q12R | V68A | N76D | S103A | V104I | G159D | Q236H | | | |
| V68A | N76D | S103A | V104I | G1S9D | Y209S | Q236H | T253K | | |
| V68A | N76D | S103A | V104I | N117K | G159D | N184S | Q236H | | |
| V68A | N76D | S103A | V104I | G159D | Q236H | N243I | | | |
| V68A | N76D | S103A | V104I | G159D | Q236H | Q245L | | | |
| V68A | N76D | S103A | V104I | A142V | G159D | | | | |
| V68A | N76D | S103A | V104I | N123S | G159D | Q236H | H249Y | | |
| V68A | N76D | S103A | V104I | G159D | Q236H | H249Q | | | |
| N76D | S103A | V104I | M222S | Q245R | | | | | |
| N76D | S103A | V104I | Q12R | M222S | H249R | | | | |
| N76D | S103A | V104I | N173R | M222S | | | | | |
| N76D | S103A | V104I | M222S | Y263F | | | | | |
| L21M | N76D | S103A | V104I | M222S | K237R | Y263F | | | |
| N76D | S103A | V104I | Q109R | M222S | | | | | |
| N76D | S103A | V104I | Q109R | M222S | E271D | | | | |
| G61R | N76D | S103A | V104I | M222S | | | | | |
| N76D | S103A | V104I | Q137R | M222S | | | | | |
| N76D | S103A | V104I | Q109R | M222S | N248S | | | | |
| N76D | S103A | V104I | M222S | H249R | | | | | |
| V68A | N76D | S103A | V104I | G159D | Q236H | Q245R | N261D | | |
| V68A | N76D | S103A | V104I | S141N | G159D | Q236H | Q245R | T255S | |
| V68A | N76D | S103A | V104I | G159D | Q236H | Q245R | R247H | | |
| V68A | N76D | S103A | V104I | G159D | A174V | N204D | Q236H | Q245R | |
| V68A | N76D | S103A | V104I | G159D | N204D | Q236H | Q245R | | |
| V68A | N76D | S103A | V104I | A133V | G159D | N218D | Q236H | Q245R | |
| V68A | N76D | S103A | V104I | G159D | A232V | Q236H | Q245R | | |
| V68A | N76D | S103A | V104I | G159D | A194I | V203A | Q236H | Q245R | |
| Q12R | N76D | S103A | V104I | M222S | Q245R | | | | |
| N76D | S103A | V104I | A232V | Q245R | | | | | |
| S24T | V68A | N76D | S103A | V104I | G159D | A232V | Q236H | Q245R | |
| V68A | S103A | V104I | G159D | A232V | Q236H | Q245R | N252K | | |
| V68A | N76D | S103A | V104I | G1S9D | T213R | A232V | Q236H | Q245R | T260A |
| Q12R | N76D | S103A | I104T | M222S | V244I | Q245R | | | |
| Q12R | N76D | S103A | M222S | P210T | Q245R | | | | |
| Q12R | N76D | S103A | I104T | S130T | M222S | Q245R | | | |
| T22K | V68A | N76D | S103A | V104I | | | | | |
| V68A | N76D | S103A | N184D | | | | | | |
| V68A | S103A | V104I | G159D | A232V | Q236H | Q245R | N248D | N252K | |
| V68A | S103A | V104I | G159D | A232V | Q236H | Q245R | | | |
| V68A | S103A | V104I | N140D | G159D | A232V | Q236H | Q245R | N252K | |
| N43S | V68A | S103A | V104I | G159D | A232V | Q236H | Q245R | N252K | |
| N43K | V68A | S103A | V104I | G159D | A232V | Q236H | Q245R | | |
| N43D | V68A | S103A | V104I | G159D | A232V | Q236H | Q245R | N252K | |
| V68A | S87G | S103A | V104I | G159D | A232V | Q236H | Q245R | N252K | R275S |
| Q12R | N76D | S103A | I104T | S130T | M222S | Q245R | N248S | L262M | |
| Q12R | N76D | S103A | I104T | S130T | A215V | M222S | Q245R | | |
| Q12R | N76D | S103A | I104T | S130T | M222S | V227A | Q245R | L2625 | |
| Q12R | N76D | S103A | I104T | S130T | A215T | M222S | Q245R | | |
| Q12R | N76D | S103A | I104T | S130T | M222S | Q245R | N261D | | |
| N76D | S103A | I104T | S130T | M222S | Q245R | | | | |
| Q12R | N76D | S103A | I104T | S130T | N218D | M222S | Q245R | L262S | N269D |
| Q12R | S57P | N76D | S103A | I104T | S130T | M222S | Q245R | K251Q | |
| Q12R | N76D | S103A | I104T | S130T | R170S | N185D | M222S | N243D | Q245R |
| Q12R | N76D | S103A | I104T | S130T | M222S | Q245R | V268A | | |
| Q12R | N76D | S103A | I104T | S130T | M222S | P2105 | Q245R | | |
| V68A | S103A | V104I | G159D | A232V | Q236H | Q245R | L257V | | |
| V68A | S103A | V104I | N116D | G159D | A232V | Q236H | Q245R | | |

TABLE 4-continued

| | | | | | | | | | | |
|---|---|---|---|---|---|---|---|---|---|---|
| V68A | S103A | V104I | G159D | A232V | Q236H | Q245R | N248D | | | |
| R10C | V68A | S103A | V104I | G159D | A232V | Q236H | Q245R | | | |
| V68A | S103A | V104I | G159D | V203E | A232V | Q236H | Q245R | | | |
| V68A | S103A | V104I | G159D | A232V | Q236H | K237E | Q245R | | | |
| V68A | N76D | I79N | S103A | V104I | G159D | A232V | Q236H | Q245R | | |
| V68A | S103A | V104I | G159D | N183D | A232V | Q236H | Q245R | | | |
| V68A | S103A | V104I | G159D | A174V | Q206L | A232V | Q236H | Q245R | | |
| V68A | S103A | V104I | G159D | S188C | A232V | Q236H | Q245R | | | |
| V68A | S103A | V104I | G159D | A230T | A232V | Q236H | Q245R | | | |
| V68A | A98T | S103A | V104I | G159D | A232V | Q236H | Q245R | | | |
| V68A | S103A | V104I | G159D | A215T | A232V | Q236H | Q245R | | | |
| V68A | S103A | V104I | G159D | A232V | Q236H | Q245R | N248S | | | |
| V68A | N76D | S103A | V104I | G159D | A232V | Q236H | Q245R | | | |
| V68A | N76D | S103A | V104I | G159D | P210R | A232V | Q236H | Q245R | | |
| V68A | N76D | S103A | V104I | G159D | A232V | Q236H | Q245R | L257V | | |
| N76D | S103A | V104I | A232V | Q236H | Q245R | L257V | | | | |
| V68A | S103A | V104I | G159D | A232V | Q236H | Q245R | L257V | R275H | | |
| N76D | S103A | V104I | L257V | R275H | | | | | | |
| V68A | S103A | V104I | G159D | T224A | A232V | Q236H | Q245R | L257V | | |
| N76D | S103A | V104I | G159D | A232V | Q236H | Q245R | L257V | | | |
| V68A | N76D | S103A | V104I | G159D | Y209W | A232V | Q236H | Q245R | | |
| V68A | N76D | S103A | V104I | G159D | G211R | A232V | Q236H | Q245R | | |
| V68A | N76D | S103A | V104I | G1S9D | G211V | A232V | Q236H | Q245R | | |
| Q12R | V68A | N76D | S103A | V104I | G159D | Y214L | A232V | Q236H | Q245R | |
| V68A | N76D | S103A | V104I | G159D | A215R | A232V | Q236H | Q245R | | |
| Q12R | V68A | N76D | S103A | V104I | G159D | A232V | Q236H | Q245R | | |
| G20R | V68A | N76D | S103A | V104I | G159D | A232V | Q236H | Q245R | S259G | |
| V68A | S87R | N76D | S103A | V104I | G159D | A232V | Q236H | Q245R | T260V | |
| V68A | N76D | S103A | V104I | G159D | A232V | Q236H | Q245R | N261G | | |
| V68A | N76D | S103A | V104I | G159D | A232V | Q236H | Q245R | N261W | | |
| N76D | S103A | V104I | A232V | Q236H | S242P | Q245R | | | | |
| V68A | N76D | S103A | V104I | G159D | P210L | A232V | Q236H | Q245R | | |
| Q12R | A48V | V68A | N76D | S103A | V104I | G159D | A232V | Q236H | Q245R | |
| N76D | S103A | V104I | A232V | Q236H | Q245R | | | | | |
| N76D | S103A | V104I | G159D | Y192F | A232V | Q236H | Q245R | | | |
| N76D | S103A | V104I | V147I | G159D | A232V | Q236H | Q245R | N2485 | K251R | |
| Q12R | V68A | N76D | S103A | V104I | G159D | A232V | Q236H | Q245R | A272S | |
| V68A | N76D | S103A | V104I | G159D | N183K | Q206L | A232V | Q236H | Q245R | |
| V68A | N76D | S103A | V104I | G159D | A232V | Q236H | Q245R | S256R | | |
| V68A | N76D | S103A | V104I | G159D | Q206R | A232V | Q236H | Q245R | | |
| K27R | V68A | N76D | S103A | V104I | G159D | A232V | Q236H | Q245R | | |
| V68A | N76D | S103A | V104I | N116T | G159D | R170S | N1855 | A232V | Q236H | Q245R |
| G61E | V68A | S103A | V104I | G159D | A232V | Q236H | Q245R | N248D | N252K | |
| N43D | V68A | S103A | V104I | G159D | A232V | Q236H | Q245R | N248D | N252K | |
| V68A | S103A | V104I | G159D | S212P | A232V | Q236H | Q245R | N248D | N252K | |
| V68A | S103A | V104I | S99N | G159D | N184D | A232V | Q236H | Q245R | N248D | N252K |
| S103A | V104I | G159D | A232V | Q236H | Q245R | N248D | N252K | | | |
| V68A | S103A | V104I | G159D | Y209W | A232V | Q236H | Q245R | N248D | N252K | |
| V68A | S103A | V104I | Q109R | G159D | A232V | Q236H | Q245R | N248D | N252K | |
| G20R | V68A | S103A | V104I | G159D | A232V | Q236H | Q245R | N2480 | N252K | |
| V68A | S103A | V104I | G159D | Y209F | A232V | Q236H | Q245R | N248D | N252K | |
| V68A | S103A | V104I | G159D | A232V | Q236H | Q245R | N248D | N252K | N261D | |
| V68A | S103A | V104I | G159D | N185D | A232V | Q236H | Q245R | N248D | N252K | |
| V68A | S103A | V104I | G159D | P210R | A232V | Q236H | Q245R | N248D | N252K | |
| V68A | S103A | V104I | G159D | P210T | A232V | Q236H | Q245R | N248D | N252K | |
| V68A | S103A | V104I | G159D | P210S | A232V | Q236H | Q245R | N248D | N252K | |
| V68A | S103A | V104I | G159D | N185D | P210L | A232V | Q236H | Q245R | N248D | N252K |
| V68A | S103A | V104I | G159D | P210L | A232V | Q236H | Q245R | N248D | N252K | |
| V68A | S103A | V104I | G159D | S212A | A232V | Q236H | Q245R | N248D | N252K | |
| V68A | S103A | V104I | G159D | S212G | A232V | Q236H | Q245R | N248D | N252K | |
| V68A | S103A | V104I | G159D | S212E | A232V | Q236H | Q245R | N248D | N252K | |
| V68A | S103A | V104I | G159D | T213E | A232V | Q236H | Q245R | N248D | N252K | |
| V68A | S103A | V104I | T213S | A232V | Q236H | Q245R | N248D | N252K | | |
| V68A | A103V | V104I | G159D | T213E | A232V | Q236H | Q245R | N248D | N252K | |
| V68A | S103A | V104I | G159D | T213R | A232V | Q236H | Q245R | N248D | N252K | |
| V68A | S103A | V104I | G159D | T213G | A232V | Q236H | Q245R | N248D | N252K | |
| V68A | S103A | V104I | G159D | A215V | A232V | Q236H | Q245R | N248D | N252K | |
| V68A | S103A | V104I | G159D | A215R | A232V | Q236H | Q245R | N248D | N252K | |
| V68A | S103A | V104I | G159D | S216T | A232V | Q236H | Q245R | N248D | N252K | |
| V68A | S103A | V104I | G159D | S216V | A232V | Q236H | Q245R | N248D | N252K | |
| V68A | S103A | V104I | G159D | S216C | A232V | Q236H | Q245R | N248D | N252K | |
| G20A | V68A | S103A | V104I | G159D | A232V | Q236H | Q245R | N248D | N252K | |
| V68A | S103A | V104I | G159D | N173D | A232V | Q236H | Q245R | N248D | N252K | |
| V68A | S103A | V104I | G159D | A232V | Q236H | Q245R | N248D | K251V | N252K | |
| V68A | S103A | V104I | G159D | Q206R | A232V | Q236H | Q245R | N248D | N252K | |
| V68A | S103A | V104I | G159D | A232V | Q236H | Q245R | N248D | N252F | | |
| V68A | S103A | V104I | G159D | A232V | Q236H | Q245R | N248D | N252L | | |
| P55S | V68A | S103A | V104I | G159D | A232V | Q236H | Q245R | N248D | N252F | |
| V68A | S103A | V104I | G159D | A232V | Q236H | Q245R | N248D | N252K | T255V | |

TABLE 4-continued

| | | | | | | | | | | | |
|---|---|---|---|---|---|---|---|---|---|---|---|
| V68A | S103A | V104I | G159D | A232V | Q236H | Q245R | N248D | N252K | S256N | | |
| V68A | S103A | V104I | G159D | A232V | Q236H | Q245R | N248D | N252K | S256E | | |
| V68A | S103A | V104I | G1S9D | A232V | Q236H | Q245R | N248D | N252K | S256R | | |
| V68A | S103A | V104I | G159D | A232V | Q236H | Q245R | N248D | N252K | T260R | | |
| V68A | S103A | V104I | G159D | A232V | Q236H | Q245R | N248D | N252K | L257R | | |
| V68A | S103A | V104I | G159D | A232V | Q236H | Q245R | N248D | N252K | G258D | | |
| I8V | V68A | S103A | V104I | G159D | A232V | Q236H | Q245R | N248D | N252K | N269D | |
| V68A | S103A | V104I | N116S | G159D | A232V | Q236H | Q245R | N248D | N252K | T260E | |
| V68A | S103A | V104I | G159D | A232V | Q236H | Q245R | N248D | N252K | N261R | | |
| V68A | S103A | V104I | G159D | A232V | Q236H | Q245R | N248D | N252K | N261D | | |
| V68A | N76D | S103A | V104I | G159D | A232V | Q236H | Q245R | N248D | N252K | | |
| V68A | S103A | V104I | A232V | Q236H | Q245R | N248D | N252K | | | | |
| S103A | V104I | G159D | A232S | Q236H | Q245R | N248D | N252K | | | | |
| V68A | S103A | V104I | G159D | A232V | Q236R | Q245R | N248D | N252K | | | |
| N18S | V68A | S103A | V104I | G159D | A232V | Q236H | Q245R | N248D | N252K | | |
| V68A | S103A | V104I | G159D | A232V | Q236H | Q245V | N248D | N252K | | | |
| V68A | N76D | S101T | S103A | V104I | G159D | T213R | N2185 | A232V | Q236H | Q245R | T260A |
| V68A | S103A | V104I | G159D | A228V | A232V | Q236H | Q245R | N248D | N252K | | |
| T33S | V68A | N76D | S103A | V104I | G159D | A232V | Q236H | Q245R | N248D | N252K | |
| V68A | N76D | E89D | S103A | V104I | G159D | P210L | T213R | A232V | Q236H | Q245R | T260A |
| G61E | V68A | N76D | S103A | V104I | G159D | A232V | Q236H | Q245R | N248D | N252K | |
| S103A | V104I | G159D | V2051 | P210I | A232V | Q236H | Q245R | | | | |
| G61E | V68A | S103A | V104I | S130A | G159D | A232V | Q236H | Q245R | N248D | N252K | |
| G61E | V68A | S103A | V104I | A133S | Q137R | G159D | A232V | Q236H | Q245R | N248D | N252K |
| G61E | S103A | V104I | A133V | G159D | A232V | Q236H | Q245R | N248D | N252K | | |
| V68A | S103A | V104I | G159D | A232V | Q236H | Q245R | N248G | N252K | | | |
| V68A | S103A | V104I | G159D | N2185 | A232V | Q236H | Q245R | N248D | N252K | | |
| G61E | V68A | S103A | V104I | G159D | S160V | A232V | Q236H | Q245R | N248D | N252K | |
| S3L | G61E | V68A | N76D | S103A | V104I | A232V | Q236H | Q245R | N248D | N252K | |
| G61E | V68A | S103A | V104I | G159D | S167F | A232V | Q236H | Q245R | N248D | N252K | |
| G97E | S103A | V104I | G159D | A232V | Q236H | Q245R | N248D | N252K | | | |
| A98D | S103A | V104I | G159D | A232V | Q236H | Q245R | N248D | N252K | | | |
| S99E | S103A | V104I | G159D | A232V | Q236H | Q245R | N248D | N252K | | | |
| S101E | S103A | V104I | G159D | A232V | Q236H | Q245R | N248D | N252K | | | |
| S101G | S103A | V104I | G159D | A232V | Q236H | Q245R | N248D | N252K | | | |
| G102A | S103A | V104I | G159D | A232V | Q236H | Q245R | N248D | N252K | | | |
| S103A | V104I | 5106E | G159D | A232V | Q236H | Q245R | N248D | N252K | | | |
| S103A | V104I | Q109E | G159D | A232V | Q236H | Q245R | N248D | N252K | | | |
| S103A | V104I | G159D | A232V | Q236H | Q245R | N248D | N252K | N261R | | | |
| S103A | V104I | Q109R | G159D | A232V | Q236H | Q245R | N248D | N252K | | | |
| N62D | S103A | V104I | G159D | A232V | Q236H | Q245R | N248D | N252K | | | |
| S103A | V104I | G159D | N184D | A232V | Q236H | Q245R | N248D | N252K | | | |
| S103A | V104I | G159D | S166D | A232V | Q236H | Q245R | N248D | N252K | | | |
| S103A | V104I | G159D | L217E | A232V | Q236H | Q245R | N248D | N252K | | | |
| G20R | N62D | S103A | V104I | G159D | T213R | A232V | Q236H | Q245R | N248D | N252K | |
| N62D | S103A | V104I | G159D | T213R | A232V | Q236H | Q245R | N248D | N252K | | |
| S103A | V104I | G159D | Q206R | L217E | A232V | Q236H | Q245R | N248D | N252K | | |
| N62D | S103A | V104I | G159D | Q206R | A232V | Q236H | Q245R | N248D | N252K | | |
| S103A | V104I | S130G | G159D | A232V | Q236H | Q245R | N248D | N252K | | | |
| S103A | V104I | P131V | G159D | A232V | Q236H | Q245R | N248D | N252K | | | |
| K27N | S103A | V104I | G159D | A232V | Q236H | Q245R | N248D | N252K | | | |
| T38G | S103A | V104I | G159D | A232V | Q236H | Q245R | N248D | N252K | | | |
| T38A | N76D | S103A | V104I | G159D | T213R | A232V | Q236H | Q245R | T260A | | |
| V68A | N76D | S103A | V104I | G159D | T213R | A232V | Q236H | Q245R | T260A | E271G | |
| V68A | N76D | S103A | V104I | G159D | Y209W | T213R | A232V | Q236H | Q245R | T260A | |
| V68A | N76D | S103A | V104I | G159D | P2101 | T213R | A232V | Q236H | Q245R | T260A | |
| V68A | N76D | S103A | V104I | G159D | V2051 | T213R | A232V | Q236H | Q245R | T260A | |
| V68A | N76D | S103A | V104I | G159D | P2101 | A232V | Q236H | Q245R | T260A | | |
| V68A | S103A | V104I | G159D | T213R | A232V | Q236H | Q245R | T260A | | | |
| N76D | S103A | V104I | G159D | T213R | A232V | Q236H | Q245R | T260A | | | |
| V68A | S103A | V104I | G159D | Y209W | A232V | Q236H | Q245R | | | | |
| V68A | S103A | V104I | G159D | P210I | A232V | Q236H | Q245R | | | | |
| V68A | S103A | V104I | G159D | A230V | A232V | Q236H | Q245R | | | | |
| V68A | S103A | V104I | G159D | L126F | A232V | Q236H | Q245R | | | | |
| V68A | S103A | V104I | G159D | V205I | A232V | Q236H | Q245R | | | | |
| V68A | S103A | V104I | G159D | P210L | A232V | Q236H | Q245R | | | | |
| S103A | V104I | G159D | A230V | Q236H | Q245R | | | | | | |
| V68A | S103A | V104I | G159D | A232V | Q236H | Q245R | T260A | | | | |
| S103A | V104I | G159D | A232V | Q236H | Q245R | | | | | | |
| V68A | S103A | V104I | G159D | A174V | A232V | Q236H | Q245R | L257V | | | |
| V68A | S103A | V104I | G159D | A194S | A232V | Q236H | Q245R | L257V | | | |
| V68A | S103A | V104I | G159D | Y209W | A232V | Q236H | Q245R | L257V | | | |
| S103A | V104I | G159D | A232V | Q236H | Q245R | L257V | | | | | |

TABLE 4-continued

| | | | | | | | | | | | | |
|---|---|---|---|---|---|---|---|---|---|---|---|---|
| V68A | N76D | S103A | V104I | G159D | T213R | A232V | Q236H | Q245R | T260A | N261W | | |
| V68A | S103A | V104I | G1S9D | A232V | Q236H | Q245R | L257V | N261W | | | | |
| S103A | V104I | G159D | T213R | A232V | Q236H | Q245R | T260A | | | | | |
| S103A | V104I | G159D | P210I | A232V | Q236H | Q245R | N248D | N252K | | | | |
| S103A | V104I | G159D | Y209W | A232V | Q236H | Q245R | L257V | | | | | |
| V68A | N76D | S103A | V104I | G159D | P210L | T213R | A232V | Q236H | Q245R | T260A | | |
| Q12R | S103A | V104I | G159D | Y209W | T213R | A232V | Q236H | Q245R | T260A | | | |
| S103A | V104I | Y209W | A232V | Q236H | Q245R | L257V | | | | | | |
| S103A | V104I | G159D | V205I | P210I | T213R | A232V | Q236H | Q245R | T260A | | | |
| S103A | V104I | G159D | V205I | Y209W | A232V | Q236H | Q245R | T260A | | | | |
| V68A | S103A | V104I | G159D | V205I | Y209W | P210I | A232V | Q236H | Q245R | | | |
| S103A | V104I | G159D | V205I | Y209W | P2101 | A232V | Q236H | Q245R | L257V | | | |
| S103A | V104I | G159D | V205I | Y209W | A232V | Q236H | Q245R | L257V | | | | |
| V68A | S103A | V104I | G159D | V205I | Y209W | P210I | A232V | Q236H | Q245R | T260A | | |
| S103A | V104I | G159D | V205I | Y209W | P210I | A232V | Q236H | Q245R | | | | |
| S103A | V104I | G159D | Y209W | P210I | A232V | Q236H | Q245R | | | | | |
| S103A | V104I | G159D | V205I | P210I | A232V | Q236H | Q245R | | | | | |
| V68A | S103A | V104I | S128L | G159D | A232V | Q236H | Q245R | | | | | |
| A48V | S103A | V104I | G159D | A230V | Q236H | Q245R | | | | | | |
| A48V | V68A | S103A | V104I | G159D | Y209W | A232V | Q236H | Q245R | | | | |
| A48V | V68A | S103A | V104I | G159D | A232V | Q236H | Q245R | N248D | N252K | | | |
| A48V | V68A | S103A | V104I | G159D | A232V | Q236H | Q245R | L257V | N261W | | | |
| G102A | S103A | V104I | G159D | S212G | A232V | Q236H | Q245R | N248D | N252K | | | |
| Q12R | G102A | S103A | V104I | G159D | S212G | A232V | Q236H | Q245R | N248D | N252K | | |
| S101G | G102A | S103A | V104I | G159D | S212G | A232V | Q236H | Q245R | N248D | N252K | | |
| A98L | G102A | S103A | V104I | G159D | S212G | A232V | Q236H | Q245R | N248D | N252K | | |
| G102A | S103A | V104I | G159D | T213R | A232V | Q236H | Q245R | N248D | N252K | | | |
| S103A | V104I | P131V | G159D | A232V | Q236H | Q245R | N248D | N252K | | | | |
| S103A | V104I | G159D | N1845 | A232V | Q236H | Q245R | N248D | N252K | | | | |
| S103A | V104I | G159D | N184G | A232V | Q236H | Q245R | N2480 | N252K | | | | |
| S103A | V104I | G159D | A232V | Q236H | V244T | Q245R | N248D | N252K | | | | |
| S103A | V104I | G159D | A232V | Q236H | V244A | Q245R | N248D | N252K | | | | |
| N62D | S103A | V104I | G159D | T213R | A232V | Q236H | Q245R | N248D | N252K | 5256R | | |
| Q12R | N62D | S103A | V104I | G159D | T213R | A232V | Q236H | Q245R | N248D | N252K | | |
| S101G | S103A | V104I | G159D | N18SD | A232V | Q236H | Q245R | N248D | N252K | | | |
| S101G | S103A | V104I | G159D | Q206E | A232V | Q236H | Q245R | N248D | N252K | | | |
| S101G | S103A | V104I | G159D | T213Q | A232V | Q236H | Q245R | N248D | N252K | | | |
| A98L | G102A | S103A | V104I | G159D | A232V | Q236H | Q245R | N248D | N252K | | | |
| S101G | G102A | S103A | V104I | G159D | A232V | Q236H | Q245R | N248D | N252K | | | |
| A98L | G102A | S103A | V104I | G159D | S212G | A232V | Q236H | Q245R | N248D | N252K | | |
| A98L | G102A | S103A | V104I | G159D | S212G | A232V | Q236H | N248D | N252K | | | |
| N62D | S103A | V104I | Q109R | G159D | T213R | A232V | Q236H | Q245R | N248D | N252K | | |
| N62D | S103A | V104I | G159D | 5212G | T213R | A232V | Q236H | Q245R | N248D | N252K | | |
| N62D | S101G | S103A | V104I | G159D | S212G | T213R | A232V | Q236H | Q245R | N248D | N252K | |
| S103A | V104I | G159D | A232V | Q245R | N248D | N252K | | | | | | |
| S103A | V104I | G159D | A230V | Q245R | | | | | | | | |
| N62D | S103A | V104I | S130G | G159D | T213R | A232V | Q236H | Q245R | N248D | N252K | | |
| S101G | S103A | V104I | 5130G | G159D | A232V | Q236H | Q245R | N248D | N252K | | | |
| S101G | S103A | V104I | 5128G | G159D | A232V | Q236H | Q245R | N248D | N252K | | | |
| S101G | S103A | V104I | 5128L | G159D | A232V | Q236H | Q245R | N248D | N252K | | | |
| N62D | S101G | S103A | V104I | G159D | T213R | A232V | Q236H | Q245R | N248D | N252K | | |
| N62D | S103A | V104I | 5128G | G159D | T213R | A232V | Q236H | Q245R | N248D | N252K | | |
| N62D | S103A | V104I | S128L | G159D | T213R | A232V | Q236H | Q245R | N248D | N252K | | |
| S101G | S103A | V104I | G1S9D | A232V | Q236H | Q245R | N248D | N252K | T260A | | | |
| S101G | S103A | V104I | P131V | G159D | A232V | Q236H | Q245R | N248D | N252K | | | |
| A98V | S101G | S103A | V104I | G159D | A232V | Q236H | Q245R | N248D | N252K | | | |
| S99G | S101G | S103A | V104I | G159D | A232V | Q236H | Q245R | N248D | N252K | | | |
| S101G | S103A | V104I | G159D | S212G | A232V | Q236H | Q245R | N248D | N252K | | | |
| S101G | S103A | V104I | G159D | Y209W | A232V | Q236H | Q245R | N248D | N252K | | | |
| S101G | S103A | V104I | G159D | P2101 | A232V | Q236H | Q245R | N248D | N252K | | | |
| S101G | S103A | V104I | G159D | V2051 | A232V | Q236H | Q245R | N248D | N252K | | | |
| S101G | S103A | V104I | G159D | A230V | Q236H | Q245R | | | | | | |
| S101G | S103A | V104I | G159D | A194P | A232V | Q236H | Q245R | N248D | N252K | | | |
| N76D | S101G | S103A | V104I | G159D | A194P | A232V | Q236H | Q245R | N248D | N252K | | |
| S101G | S103A | V104I | G159D | A230V | A232V | Q236H | Q245R | N248D | N252K | | | |
| N62D | S103A | V104I | G159D | N185D | Q206E | T213R | A232V | Q236H | Q245R | N248D | N252K | E271Q |

EXAMPLE 2

A large number of the protease variants produced in Example 1 were tested for performance in two types of detergent and wash conditions using a microswatch assay described in "An improved method of assaying for a preferred enzyme and/or preferred detergent composition", U.S. Ser. No. 60/068,796.

Table 5 lists the variant proteases assayed and the results of testing in two different detergents. For column A, the detergent was 0.67 g/l filtered Ariel Ultra (Procter & Gamble, Cincinnati, Ohio, USA), in a solution containing 3 grains per gallon mixed $Ca^{2+}/Mg^{2+}$ hardness, and 0.3 ppm enzyme was used in each well at 20° C. For column B, the detergent was 3.38 g/l filtered Ariel Futur (Procter & Gamble, Cincinnati, Ohio, USA), in a solution containing 15 grains per gallon mixed $Ca^{2+}/Mg^{2+}$ hardness, and 0.3 ppm enzyme was used in each well at 40° C.

TABLE 5

| | | | | | | | | | | A | B |
|---|---|---|---|---|---|---|---|---|---|---|---|
| N76D | S103A | V104I | | | | | | | | 1 | 1 |
| S103A | V104I | A228T | | | | | | | | 0.56 | 1.11 |
| V68A | S103A | V104I | G159D | A232V | Q236H | Q245R | N252K | | | 1.41 | 1.85 |
| V68A | S103A | V104I | G159D | A232V | Q236H | Q245R | N248D | N252K | | 2.77 | 1.20 |
| V68A | S103A | V104I | G159D | A232V | Q236H | Q245R | | | | 2.26 | 1.67 |
| V68A | S103A | V104I | N140D | G159D | A232V | Q236H | Q245R | N252K | | 2.96 | 1.42 |
| N43S | V68A | S103A | V104I | G159D | A232V | Q236H | Q245R | N252K | | 1.91 | 1.80 |
| N43K | V68A | S103A | V104I | G159D | A232V | Q236H | Q245R | | | 2.05 | 1.78 |
| N43D | V68A | S103A | V104I | G159D | A232V | Q236H | Q245R | N252K | | 2.00 | 1.34 |
| V68A | S103A | V104I | G159D | A232V | Q236H | Q245R | L257V | | | 2.38 | 1.67 |
| V68A | S103A | V104I | G159D | A232V | Q236H | Q245R | N248D | | | 2.83 | 0.53 |
| V68A | S103A | V104I | G159D | A232V | Q236H | K237E | Q245R | | | 2.87 | 0.20 |
| V68A | S103A | V104I | G159D | A232V | Q236H | Q245R | N252S | | | 2.56 | 1.41 |
| V68A | S103A | V104I | G159D | A232V | Q236H | Q245R | L257V | R275H | | 3.97 | 0.47 |
| V68A | S103A | V104I | G159D | T224A | A232V | Q236H | Q245R | L257V | | 3.35 | 1.28 |
| G61E | V68A | S103A | V104I | G159D | A232V | Q236H | Q245R | N248D | N252K | 3.77 | 0.09 |
| N43D | V68A | S103A | V104I | G159D | A232V | Q236H | Q245R | N248D | N252K | 3.50 | 0.47 |
| V68A | S103A | V104I | G159D | S212P | A232V | Q236H | Q245R | N248D | N252K | 2.81 | 1.46 |
| N76D | A98E | S103A | V104I | | | | | | | 1.56 | 0.28 |
| V4E | N76D | S103A | V104I | | | | | | | 1.22 | 0.33 |
| N76D | N77D | S103A | V104I | | | | | | | 1.13 | 0.36 |
| A16T | N76D | S103A | V104I | N248D | | | | | | 1.22 | 0.43 |
| A1E | N76D | S103A | V104I | | | | | | | 1.12 | 0.32 |
| N76D | S103A | V104I | N261D | | | | | | | 1.54 | 0.33 |
| N76D | S103A | V104I | S216C | | | | | | | 1.04 | 0.13 |
| N76D | N77D | S103A | V104I | A174V | | | | | | 1.09 | 0.35 |
| T38S | N76D | S103A | V104I | K237Q | | | | | | 1.11 | 0.55 |
| N76D | S103A | V104I | N183D | | | | | | | 1.50 | 0.25 |
| R19L | N76D | S103A | V104I | | | | | | | 1.11 | 0.48 |
| R19C | N76D | S103A | V104I | | | | | | | 1.05 | 0.19 |
| N76D | S103A | V104I | N184D | | | | | | | 1.32 | 0.29 |
| N76D | S103A | V104I | N252D | | | | | | | 1.19 | 0.53 |
| N76D | S103A | V104I | S259C | | | | | | | 0.92 | 0.12 |
| N76D | S103A | V104I | K251T | | | | | | | 1.31 | 0.43 |
| N76D | P86S | S103A | V104I | | | | | | | 1.00 | 0.98 |
| I72V | N76D | S103A | V104I | N185D | | | | | | 1.70 | 0.37 |
| N76D | S103A | V104I | K237E | T274A | | | | | | 1.12 | 0.16 |
| N76D | S103A | V104I | A228V | | | | | | | 1.13 | 0.99 |
| N76D | S103A | V104I | G159D | | | | | | | 1.88 | 0.23 |
| H17L | N76D | S103A | V104I | K237E | | | | | | 1.29 | 0.28 |
| N76D | S103A | V104I | S130L | | | | | | | 0.52 | 0.71 |
| N76D | S103A | V104I | Q109R | | | | | | | 0.23 | 1.26 |
| N76D | S99R | S103A | V104I | N204T | | | | | | 0.21 | 0.87 |
| N76D | S103A | V104I | D181N | | | | | | | 0.24 | 1.07 |
| Q12R | N76D | S103A | V104I | | | | | | | 0.61 | 1.31 |
| N76D | S103A | V104I | S212P | E271V | | | | | | 0.69 | 1.35 |
| N76D | S103A | V104I | N252K | N261Y | | | | | | 0.37 | 1.02 |
| N76D | S103A | V104I | S242T | | | | | | | 0.98 | 0.92 |
| N76D | S103A | V104I | E271Q | | | | | | | 0.63 | 1.25 |
| Q12R | N76D | S103A | V104I | S242T | | | | | | 0.49 | 1.32 |
| N43S | N76D | S103A | V104I | N116K | N183I | | | | | 0.39 | 1.10 |
| N76D | S103A | V104I | G258R | | | | | | | 0.34 | 1.17 |
| N76D | S103A | V104I | E271G | | | | | | | 0.57 | 1.25 |
| N76D | S103A | V104I | Q182R | I198V | | | | | | 0.22 | 0.95 |
| L21M | N76D | S103A | V104I | Q182R | | | | | | 0.24 | 0.98 |
| N76D | S103A | V104I | M119I | Q137R | | | | | | 0.13 | 0.91 |
| N76D | S103A | V104I | Q137R | N248S | | | | | | 0.16 | 1.02 |
| A13T | N76D | S103A | V104I | Q206R | | | | | | 0.31 | 1.01 |
| N76D | S103A | V104I | Q206R | | | | | | | 0.33 | 1.02 |
| N76D | S103A | V104I | S212P | G258R | | | | | | 0.38 | 1.06 |
| T58S | N76D | S103A | V104I | E271G | | | | | | 0.84 | 1.26 |
| N76D | S103A | V104I | Q206E | N261D | | | | | | 1.97 | 0.04 |
| V4E | N76D | S103A | V104I | Q206E | | | | | | 1.51 | 0.05 |
| N76D | N77D | S103A | V104I | Q206E | | | | | | 1.40 | 0.04 |
| N76D | S103A | V104I | A158E | | | | | | | 1.95 | 0.16 |
| N76D | S103A | V104I | Q206E | | | | | | | 2.41 | 0.88 |
| N76D | N77D | S103A | V104I | A133T | N185D | K251T | | | | 1.34 | 0.03 |
| N76D | S103A | V104I | Q206E | N261D | | | | | | 1.78 | 0.04 |
| N76D | S103A | V104I | G159D | Q206E | V244A | | | | | 2.16 | 0.04 |
| V4E | N76D | S103A | V104I | S188E | | | | | | 1.91 | 0.04 |
| V4E | N76D | S103A | V104I | A158E | | | | | | 2.06 | 0.04 |
| N76D | S103A | V104I | Q206E | K251T | | | | | | 1.73 | 0.06 |
| A48T | N76D | S103A | V104I | L111M | G159D | | | | | 2.04 | 0.16 |
| V68A | N76D | S103A | V104I | G159D | Q236H | | | | | 3.20 | 0.09 |
| L42V | N76D | S103A | V104I | G159D | | | | | | 1.83 | 0.17 |
| Q12H | N62H | N76D | S103A | V104I | G159D | | | | | 1.42 | 0.14 |
| L42I | N76D | S103A | V104I | G159D | | | | | | 1.86 | 0.18 |

TABLE 5-continued

| | | | | | | | | | | | A | B |
|---|---|---|---|---|---|---|---|---|---|---|---|---|
| N76D | S103A | V104I | G146S | G159D | | | | | | | 1.87 | 0.19 |
| N76D | S103A | V104I | G159D | N238S | | | | | | | 1.90 | 0.15 |
| N76D | S103A | V104I | G159D | T224A | | | | | | | 1.61 | 0.07 |
| N76D | S103A | V104I | S212P | V268F | E271V | | | | | | 0.44 | 1.42 |
| N76D | S87R | S103A | V104I | S212P | E271V | | | | | | 0.39 | 2.03 |
| N76D | S103A | V104I | S212P | Q245L | E271V | | | | | | 0.62 | 1.79 |
| N76D | S103A | V104I | Q109R | Q245R | | | | | | | 0.11 | 1.78 |
| N76D | S103A | V104I | Q109R | P210L | | | | | | | 0.12 | 1.21 |
| G20V | N62S | N76D | S103A | V104I | | | | | | | 1.63 | 0.78 |
| V68A | N76D | S103A | V104I | Q236H | | | | | | | 2.37 | 0.44 |
| V68A | N76D | S103A | V104I | G159D | Q236H | E271V | | | | | 2.97 | 0.45 |
| V68A | N76D | S103A | V104I | G159D | Q236H | Q245R | | | | | 3.00 | 0.61 |
| V68A | N76D | S103A | V104I | G159D | L217I | Q236H | E271V | | | | 2.71 | 0.12 |
| H17Q | V68A | N76D | S103A | V104I | | | | | | | 2.46 | 0.38 |
| V68A | N76D | S103A | V104I | | | | | | | | 2.46 | 0.61 |
| V68A | N76D | S103A | V104I | G159D | Q236R | | | | | | 3.31 | 0.11 |
| V68A | L75R | N76D | S103A | V104I | G159D | Q236H | | | | | 3.06 | 0.14 |
| V68A | N76D | S103A | V104I | A114V | V121I | G159D | Q236H | Q245R | | | 3.11 | 0.40 |
| Q12R | V68A | N76D | S103A | V104I | G159D | Q236H | | | | | 3.12 | 0.34 |
| V68A | N76D | S103A | V104I | G159D | Y209S | Q236H | T253K | | | | 3.18 | 0.03 |
| V68A | N76D | S103A | V104I | N117K | G159D | N184S | Q236H | | | | 2.78 | 0.06 |
| V68A | N76D | S103A | V104I | Q236H | | | | | | | 2.49 | 0.57 |
| V68A | N76D | S103A | V104I | G159D | Q236H | Q245L | | | | | 3.37 | 0.03 |
| V68A | N76D | S103A | V104I | N123S | G159D | Q236H | H249Y | | | | 3.11 | 0.03 |
| V68A | N76D | S103A | V104I | G159D | Q236H | H249Q | | | | | 3.15 | 0.04 |
| V68A | N76D | S103A | V104I | G159D | Q236H | Q245R | N261D | | | | 3.31 | 0.03 |
| V68A | N76D | S103A | V104I | S141N | G159D | Q236H | Q245R | T255S | | | 3.26 | 0.62 |
| V68A | N76D | S103A | V104I | G159D | Q236H | Q245R | R247H | | | | 2.78 | 0.03 |
| V68A | N76D | S103A | V104I | G159D | A174V | N204D | Q236H | Q245R | | | 3.28 | 0.02 |
| V68A | N76D | S103A | V104I | G159D | N204D | Q236H | Q245R | | | | 3.34 | 0.02 |
| V68A | N76D | S103A | V104I | A133V | G159D | N218D | Q236H | Q245R | | | 3.28 | 0.03 |
| V68A | N76D | S103A | V104I | G159D | A232V | Q236H | Q245R | | | | 2.91 | 0.58 |
| V68A | N76D | S103A | V104I | G159D | A194I | V203A | Q236H | Q245R | | | 2.86 | 0.13 |
| V68A | N76D | S103A | V104I | G159D | T213R | A232V | Q236H | Q245R | T260A | | 1.30 | 1.73 |
| T22K | V68A | N76D | S103A | V104I | | | | | | | 1.83 | 1.13 |
| V68A | N76D | S103A | V104I | G159D | P210R | A232V | Q236H | Q245R | | | 1.28 | 1.54 |
| V68A | N76D | S103A | V104I | G159D | A232V | Q236H | Q245R | L257V | | | 3.72 | 0.8 |
| N76D | S103A | V104I | A232V | Q236H | Q245R | L257V | | | | | 0.6 | 1.5 |
| N76D | S103A | V104I | L257V | R275H | | | | | | | 1.91 | 0.15 |
| N76D | S103A | V104I | G159D | A232V | Q236H | Q245R | L257V | | | | 1.92 | 1.09 |
| V68A | N76D | S103A | V104I | G159D | Y209W | A232V | Q236H | Q245R | | | 3.57 | 0.99 |
| V68A | N76D | S103A | V104I | G159D | G211R | A232V | Q236H | Q245R | | | 1.74 | 1.76 |
| V68A | N76D | S103A | V104I | G159D | G211V | A232V | Q236H | Q245R | | | 3.15 | 1.06 |
| Q12R | V68A | N76D | S103A | V104I | G159D | Y214L | A232V | Q236H | Q245R | | 2.33 | 1.92 |
| V68A | N76D | S103A | V104I | G159D | A215R | A232V | Q236H | Q245R | | | 1.67 | 1.45 |
| Q12R | V68A | N76D | S103A | V104I | G159D | A232V | Q236H | Q245R | | | 2.16 | 1.72 |
| G20R | V68A | N76D | S103A | V104I | G159D | A232V | Q236H | Q245R | S259G | | 2.77 | 1.59 |
| V68A | N76D | S87R | S103A | V104I | G159D | A232V | Q236H | Q245R | T260V | | 2.62 | 1.49 |
| V68A | N76D | S103A | V104I | G159D | A232V | Q236H | Q245R | N261G | | | 2.92 | 0.68 |
| V68A | N76D | S103A | V104I | G159D | A232V | Q236H | Q245R | N261W | | | 2.17 | 1.37 |
| N76D | S103A | V104I | A232V | Q236H | S242P | Q245R | | | | | 0.48 | 1.2 |
| V68A | N76D | S103A | V104I | G159D | P210L | A232V | Q236H | Q245R | | | 2.92 | 0.76 |
| Q12R | A48V | V68A | N76D | S103A | V104I | G159D | A232V | Q236H | Q245R | | 2.09 | 1.86 |
| N76D | S103A | V104I | A232V | Q236H | Q245R | | | | | | 0.51 | 1.44 |
| N76D | S103A | V104I | G159D | Y192F | A232V | Q236H | Q245R | | | | 1.60 | 1.14 |
| N76D | S103A | V104I | V147I | G159D | A232V | Q236H | Q245R | N248S | K251R | | 1.35 | 1.29 |
| Q12R | V68A | N76D | S103A | V104I | G159D | A232V | Q236H | Q245R | A272S | | 1.92 | 1.81 |
| V68A | N76D | S103A | V104I | G159D | N183K | Q206L | A232V | Q236H | Q245R | | 1.17 | 1.53 |
| V68A | N76D | S103A | V104I | G159D | A232V | Q236H | Q245R | S256R | | | 2.01 | 1.72 |
| V68A | N76D | S103A | V104I | G159D | Q206R | A232V | Q236H | Q245R | | | 2.09 | 1.62 |
| K27R | V68A | N76D | S103A | V104I | G159D | A232V | Q236H | Q245R | | | 3.00 | 1.08 |
| V68A | N76D | S103A | V104I | N116T | G159D | R170S | N185S | A232V | Q236H | Q245R | ND | ND |
| N76D | S103A | V104I | M222S | Q245R | | | | | | | 1.01 | 1.23 |
| Q12R | N76D | S103A | V104I | M222S | H249R | | | | | | 0.57 | 1.65 |
| N76D | S103A | V104I | N173R | M222S | | | | | | | 0.86 | 0.46 |
| N76D | S103A | V104I | M222S | Y263F | | | | | | | 1.24 | 0.77 |
| L21M | N76D | S103A | V104I | M222S | K237R | Y263F | | | | | 1.18 | 0.76 |
| N76D | S103A | V104I | Q109R | M222S | | | | | | | 0.52 | 1.16 |
| N76D | S103A | V104I | Q109R | M222S | E271D | | | | | | 0.56 | 1.12 |
| G61R | N76D | S103A | V104I | M222S | | | | | | | 0.43 | 0.96 |
| N76D | S103A | V104I | Q137R | M222S | | | | | | | 0.42 | 1.25 |
| N76D | S103A | V104I | M222S | H249R | | | | | | | 1.15 | 1.01 |
| Q12R | N76D | S103A | V104I | M222S | Q245R | | | | | | 0.53 | 1.46 |
| N76D | S103A | V104I | A232V | Q245R | | | | | | | 0.69 | 1.56 |
| Q12R | N76D | S103A | I104T | M222S | V244I | Q245R | | | | | 0.66 | 1.74 |
| Q12R | N76D | S103A | V104I | M222S | P210T | Q245R | | | | | 0.52 | 1.56 |
| Q12R | N76D | S103A | I104T | S130T | M222S | Q245R | | | | | 0.70 | 1.61 |

TABLE 5-continued

| | | | | | | | | | | A | B |
|---|---|---|---|---|---|---|---|---|---|---|---|
| Q12R | N76D | S103A | I104T | S130T | A215V | M222S | Q245R | | | 0.79 | 1.85 |
| Q12R | N76D | S103A | I104T | S130T | M222S | V227A | Q245R | L262S | | 0.78 | 1.56 |
| Q12R | N76D | S103A | I104T | S130T | M222S | Q245R | N261D | | | 1.25 | 1.30 |
| N76D | S103A | I104T | S130T | M222S | Q245R | | | | | 1.29 | 1.30 |
| Q12R | S57P | N76D | S103A | I104T | S130T | M222S | Q245R | K251Q | | 1.44 | 0.16 |
| Q12R | N76D | S103A | I104T | S130T | R170S | N185D | M222S | N243D | Q245R | 2.01 | 0.04 |
| Q12R | N76D | S103A | I104T | S130T | M222S | Q245R | V268A | | | 0.77 | 1.60 |
| Q12R | N76D | S103A | I104T | S130T | M222S | P210S | Q245R | | | 0.73 | 1.66 |
| V68A | N76D | S103A | V104I | G159D | A232V | Q236H | Q245R | | | 2.09 | 0.86 |

EXAMPLE 3

Table 6 lists the variant proteases assayed from Example 1 and the results of testing in four different detergents. The same performance tests as in Example 2 were done on the noted variant proteases with the following detergents. For column A, the detergent was 0.67 g/l filtered Ariel Ultra (Procter & Gamble, Cincinnati, Ohio, USA), in a solution containing 3 grains per gallon mixed $Ca^{2+}/Mg^{2+}$ hardness, and 0.3 ppm enzyme was used in each well at 20° C. For column B, the detergent was 3.38 g/l filtered Ariel Futur (Procter & Gamble, Cincinnati, Ohio, USA), in a solution containing 15 grains per gallon mixed $Ca^{2+}/Mg^{2+}$ hardness, and 0.3 ppm enzyme was used in each well at 40° C. For column C, 3.5g/l HSP1 detergent (Procter & Gamble, Cincinnati, Ohio, USA), in a solution containing 8 grains per gallon mixed $Ca^{2+}/Mg^{2+}$ hardness, and 0.3 ppm enzyme was used in each well at 20° C. For column D, 1.5 ml/l Tide KT detergent (Procter & Gamble, Cincinnati, Ohio, USA), in a solution containing 3 grains per gallon mixed $Ca^{2+}/Mg^{2+}$ hardness, and 0.3 ppm enzyme was used in each well at 20° C.

TABLE 6

| | | | | | | | | | | | | A | B | C | D |
|---|---|---|---|---|---|---|---|---|---|---|---|---|---|---|---|
| N76D | S103A | V104I | | | | | | | | | | 1 | 1 | 1 | 1 |
| S103A | V104I | G159D | A232V | Q236H | Q245R | N248D | N252K | | | | | 1.44 | 1.41 | 1.39 | 1.26 |
| V68A | S103A | V104I | G159D | Y209W | A232V | Q236H | Q245R | N248D | N252K | | | 2.34 | 1.49 | 1.65 | 2.35 |
| V68A | S103A | V104I | Q109R | G159D | A232V | Q236H | Q245R | N248D | N252K | | | 1.05 | 1.41 | 1.20 | 1.19 |
| G20R | V68A | S103A | V104I | G159D | A232V | Q236H | Q245R | N248D | N252K | | | 1.81 | 1.72 | 1.66 | 1.31 |
| V68A | S103A | V104I | G159D | Y209F | A232V | Q236H | Q245R | N248D | N252K | | | 2.19 | 1.38 | 1.60 | 2.02 |
| V68A | S103A | V104I | G159D | N185D | A232V | Q236H | Q245R | N248D | N252K | | | 2.91 | 0.91 | 1.48 | 2.70 |
| V68A | S103A | V104I | G159D | P210R | A232V | Q236H | Q245R | N248D | N252K | | | 0.93 | 1.39 | 1.23 | 0.80 |
| V68A | S103A | V104I | G159D | N185D | P210L | A232V | Q236H | Q245R | N248D | N252K | | 2.67 | 0.86 | 1.41 | 2.88 |
| V68A | S103A | V104I | G159D | P210L | A232V | Q236H | Q245R | N248D | N252K | | | 2.22 | 1.43 | 1.55 | 1.78 |
| V68A | S103A | V104I | G159D | S212C | A232V | Q236H | Q245R | N248D | N252K | | | 2.30 | 1.43 | 1.63 | 2.07 |
| V68A | S103A | V104I | G159D | S212G | A232V | Q236H | Q245R | N248D | N252K | | | 2.31 | 1.47 | 1.62 | 2.01 |
| V68A | S103A | V104I | G159D | S212E | A232V | Q236H | Q245R | N248D | N252K | | | 2.63 | 0.56 | 1.36 | 2.66 |
| V68A | S103A | V104I | G159D | T213E | A232V | Q236H | Q245R | N248D | N252K | | | 2.75 | 0.50 | 1.27 | 2.78 |
| V68A | S103A | V104I | T213S | A232V | Q236H | Q245R | N248D | N252K | | | | 1.11 | 1.38 | 1.31 | 0.75 |
| V68A | A103V | V104I | G159D | T213E | A232V | Q236H | Q245R | N248D | N252K | | | 2.27 | 0.15 | 1.12 | 2.01 |
| V68A | S103A | V104I | G159D | T213R | A232V | Q236H | Q245R | N248D | N252K | | | 1.37 | 1.42 | 1.37 | 1.06 |
| V68A | S103A | V104I | G159D | A215V | A232V | Q236H | Q245R | N248D | N252K | | | 2.14 | 1.40 | 1.53 | 1.54 |
| V68A | S103A | V104I | G159D | A215R | A232V | Q236H | Q245R | N248D | N252K | | | 1.22 | 1.58 | 1.47 | 1.20 |
| V68A | S103A | V104I | G159D | S216T | A232V | Q236H | Q245R | N248D | N252K | | | 2.12 | 1.36 | 1.56 | 1.56 |
| V68A | S103A | V104I | G159D | S216V | A232V | Q236H | Q245R | N248D | N252K | | | 1.88 | 1.36 | 1.47 | 1.87 |
| V68A | S103A | V104I | G159D | S216C | A232V | Q236H | Q245R | N248D | N252K | | | 2.24 | 0.33 | 1.07 | 2.89 |
| V68A | S103A | V104I | G159D | N173D | A232V | Q236H | Q245R | N248D | N252K | | | 2.43 | 0.46 | 1.29 | 2.42 |
| V68A | S103A | V104I | G159D | Q206R | A232V | Q236H | Q245R | N248D | N252K | | | 0.98 | 1.46 | 1.24 | 0.95 |
| V68A | S103A | V104I | G159D | A232V | Q236H | Q245R | N248D | N252F | | | | 2.52 | 1.00 | 1.42 | 2.42 |
| V68A | S103A | V104I | G159D | A232V | Q236H | Q245R | N248D | N252L | | | | 2.05 | 1.13 | 1.30 | 1.85 |
| P55S | V68A | S103A | V104I | G159D | A232V | Q236H | Q245R | N248D | N252F | | | 2.61 | 0.91 | 1.43 | 3.22 |
| V68A | S103A | V104I | G159D | A232V | Q236H | Q245R | N248D | N252K | T255V | | | 2.18 | 1.36 | 1.58 | 1.72 |
| V68A | S103A | V104I | G159D | A232V | Q236H | Q245R | N248D | N252K | S256N | | | 2.14 | 1.46 | 1.59 | 1.65 |
| V68A | S103A | V104I | G159D | A232V | Q236H | Q245R | N248D | N252K | S256E | | | 2.46 | 0.77 | 1.33 | 2.58 |
| V68A | S103A | V104I | G159D | A232V | Q236H | Q245R | N248D | N252K | S256R | | | 1.31 | 1.52 | 1.46 | 0.94 |
| V68A | S103A | V104I | G159D | A232V | Q236H | Q245R | N248D | N252K | T260R | | | 1.21 | 1.41 | 1.31 | 1.05 |
| V68A | S103A | V104I | GIS9D | A232V | Q236H | Q245R | N248D | N252K | L257R | | | 1.51 | 1.41 | 0.85 | 1.18 |
| V68A | S103A | V104I | G159D | A232V | Q236H | Q245R | N248D | N252K | G258D | | | 2.56 | 0.59 | 1.30 | 2.64 |
| V68A | S103A | V104I | G159D | A232V | Q236H | Q245R | N248D | N252K | N261R | | | 1.02 | 1.47 | 1.37 | 0.84 |
| V68A | S103A | V104I | A232V | Q236H | Q245R | N248D | N252K | | | | | 1.04 | 1.50 | 1.32 | 0.73 |
| V68A | S103A | V104I | G159D | A232V | Q236H | Q245V | N248D | N252K | | | | 2.60 | 0.93 | 1.41 | 2.67 |
| V68A | S103A | V104I | G159D | A228V | A232V | Q236H | Q245R | N248D | N252K | | | 2.31 | 1.38 | 1.53 | 1.57 |
| G61E | V68A | S103A | V104I | S130A | G159D | A232V | Q236H | Q245R | N248D | N252K | | 2.83 | 0.25 | 1.33 | 2.44 |
| G61E | S103A | V104I | A133V | G159D | A232V | Q236H | Q245R | N248D | N252K | | | 2.10 | 0.97 | 1.36 | 2.29 |
| V68A | S103A | V104I | G159D | A232V | Q236H | Q245R | N248G | N252K | | | | 1.37 | 1.54 | 0.89 | 1.27 |
| V68A | S103A | V104I | G159D | N218S | A232V | Q236H | Q245R | N248D | N252K | | | 2.30 | 1.50 | 1.62 | 1.56 |
| G20R | V68A | S103A | V104I | G159D | A232V | Q236H | Q245R | N248D | N252K | | | 1.72 | 1.72 | 1.67 | 1.15 |
| V68A | N76D | E89D | S103A | V104I | G159D | P210L | T213R | A232V | Q236H | Q245R | T260A | 1.32 | 1.30 | 1.11 | 1.28 |
| V68A | N76D | S103A | V104I | G159D | A232V | Q236H | Q245R | N248D | N252K | | | 2.50 | 0.83 | 1.43 | 2.25 |
| G61E | V68A | S103A | V104I | G159D | 5160V | A232V | Q236H | Q245R | N248D | N252K | | 4.20 | 0.07 | ND | 1.28 |
| S3L | G61E | V68A | N76D | S103A | V104I | A232V | Q236H | Q245R | N248D | N252K | | 3.47 | 0.60 | ND | 1.45 |
| G61E | V68A | S103A | V104I | G159D | Y167F | A232V | Q236H | Q245R | N248D | N252K | | 4.32 | 0.79 | ND | 1.55 |
| G97E | S103A | V104I | G159D | A232V | Q236H | Q245R | N248D | N252K | | | | 3.14 | 0.41 | ND | 1.40 |

TABLE 6-continued

| | | | | | | | | | | | | | | | | |
|---|---|---|---|---|---|---|---|---|---|---|---|---|---|---|---|---|
| A98D | S103A | V104I | G159D | A232V | Q236H | Q245R | N248D | N252K | | | | | 2.71 | 0.68 | ND | 1.72 |
| S99E | S103A | V104I | G159D | A232V | Q236H | Q245R | N248D | N252K | | | | | 2.97 | 0.68 | ND | 1.71 |
| S101E | S103A | V104I | G159D | A232V | Q236H | Q245R | N248D | N252K | | | | | 3.50 | 0.27 | ND | 1.90 |
| S101G | S103A | V104I | G159D | A232V | Q236H | Q245R | N248D | N252K | | | | | 2.24 | 1.80 | ND | 1.33 |
| G102A | S103A | V104I | G159D | A232V | Q236H | Q245R | N248D | N252K | | | | | 3.35 | 1.33 | ND | 1.69 |
| S103A | V104I | S106E | G159D | A232V | Q236H | Q245R | N248D | N252K | | | | | 4.88 | 0.55 | ND | 2.71 |
| S103A | V104I | Q109E | G159D | A232V | Q236H | Q245R | N248D | N252K | | | | | 4.22 | 1.05 | ND | 2.40 |
| S103A | V104I | G159D | A232V | Q236H | Q245R | N248D | N252K | N261R | | | | | 5.45 | 2.19 | ND | 2.58 |
| S103A | V104I | Q109R | G159D | A232V | Q236H | Q245R | N248D | N252K | | | | | 3.76 | 2.16 | ND | 1.82 |
| N62D | S103A | V104I | G159D | A232V | Q236H | Q245R | N248D | N252K | | | | | 7.42 | 0.13 | ND | 2.46 |
| S103A | V104I | G159D | N184D | A232V | Q236H | Q245R | N248D | N252K | | | | | 5.43 | 1.36 | ND | 2.84 |
| S103A | V104I | G159D | 5166D | A232V | Q236H | Q245R | N248D | N252K | | | | | 5.12 | 1.21 | ND | 3.97 |
| S103A | V104I | G159D | L217E | A232V | Q236H | Q245R | N248D | N252K | | | | | 6.38 | 0.95 | ND | 3.09 |
| G20R | N62D | S103A | V104I | G159D | T213R | A232V | Q236H | Q245R | N248D | N252K | | | 3.17 | 2.83 | ND | 2.60 |
| N62D | S103A | V104I | G159D | T213R | A232V | Q236H | Q245R | N248D | N252K | | | | 4.38 | 1.92 | ND | 2.54 |
| S103A | V104I | G159D | Q206R | L217E | A232V | Q236H | Q245R | N248D | N252K | | | | 3.05 | 2.61 | ND | 1.10 |
| N62D | S103A | V104I | G159D | Q206R | A232V | Q236H | Q245R | N248D | N252K | | | | 4.09 | 2.46 | ND | 2.55 |
| S103A | V104I | G159D | N184G | A232V | Q236H | Q245R | N248D | N252K | | | | | 2.32 | 2.08 | ND | 2.40 |
| S103A | V104I | G159D | A232V | Q236H | V244T | Q245R | N248D | N252K | | | | | 2.34 | 2.04 | ND | 1.86 |
| S103A | V104I | G159D | A232V | Q236H | V244A | Q245R | N248D | N252K | | | | | 2.24 | 2.11 | ND | 1.95 |
| K27N | S103A | V104I | G159D | A232V | Q236H | Q245R | N248D | N252K | | | | | 2.81 | 1.56 | ND | 2.47 |
| T38G | S103A | V104I | GIS9D | A232V | Q236H | Q245R | N248D | N252K | | | | | 2.30 | 2.09 | ND | 1.82 |
| N62D | S103A | V104I | G159D | T213R | A232V | Q236H | Q245R | N248D | N252K | S256R | | | 2.63 | 2.66 | ND | 1.44 |
| Q12R | N62D | S103A | V104I | G159D | T213R | A232V | Q236H | Q245R | N248D | N252K | | | 2.01 | 2.78 | ND | 1.99 |
| N62D | S103A | V104I | G159D | N185D | Q206E | T213R | A232V | Q236H | Q245R | N248D | N252K | E271Q | 7.74 | 0.94 | ND | 5.39 |
| S101G | S103A | V104I | G159D | N185D | A232V | Q236H | Q245R | N248D | N252K | | | | 5.14 | 1.41 | ND | 1.92 |
| S101G | S103A | V104I | G159D | Q206E | A232V | Q236H | Q245R | N248D | N252K | | | | 4.97 | 0.57 | ND | 1.36 |
| S101G | S103A | V104I | G159D | T213Q | A232V | Q236H | Q245R | N248D | N252K | | | | 2.41 | 1.86 | ND | 1.01 |
| A98L | G102A | S103A | V104I | G159D | A232V | Q236H | Q245R | N248D | N252K | | | | 4.42 | 0.50 | ND | 2.88 |
| S101G | G102A | S103A | V104I | G159D | A232V | Q236H | Q245R | N248D | N252K | | | | 5.86 | 1.20 | ND | 3.84 |
| G102A | S103A | V104I | G159D | S212G | A232V | Q236H | Q245R | N248D | N252K | | | | 5.87 | 2.10 | ND | 3.19 |
| Q12R | G102A | S103A | V104I | G159D | S212G | A232V | Q236H | Q245R | N248D | N252K | | | 2.98 | 2.67 | ND | 2.17 |
| A98L | G102A | S103A | V104I | G159D | S212G | A232V | Q236H | Q245R | N248D | N252K | | | 4.02 | 0.41 | ND | 2.25 |
| S101G | G102A | S103A | V104I | G159D | S212G | A232V | Q236H | Q245R | N248D | N252K | | | 6.63 | 2.07 | ND | 2.08 |
| G102A | S103A | V104I | G159D | T213R | A232V | Q236H | Q245R | N248D | N252K | | | | 2.03 | 2.48 | ND | 2.25 |
| N62D | S103A | V104I | Q109R | G159D | T213R | A232V | Q236H | Q245R | N248D | N252K | | | 2.96 | 2.76 | ND | 2.34 |
| S103A | V104I | G159D | A232V | Q245R | N248D | N252K | | | | | | | 2.74 | 2.10 | ND | 1.86 |
| S103A | V104I | G159D | A230V | Q245R | | | | | | | | | 2.11 | 2.35 | ND | 1.49 |
| N62D | S103A | V104I | S130G | G159D | T213R | A232V | Q236H | Q245R | N248D | N252K | | | 3.42 | 0.71 | ND | 2.58 |
| S101G | S103A | V104I | S130G | G159D | A232V | Q236H | Q245R | N248D | N252K | | | | 2.59 | 1.32 | ND | 1.61 |
| S101G | S103A | V104I | S128G | G159D | A232V | Q236H | Q245R | N248D | N252K | | | | 1.30 | 1.23 | ND | 9.0 |
| S101G | S103A | V104I | S128L | G159D | A232V | Q236H | Q245R | N248D | N252K | | | | 2.94 | 0.71 | ND | 1.08 |
| N62D | S101G | S103A | V104I | G159D | T213R | A232V | Q236H | Q245R | N248D | N252K | | | 3.17 | 0.83 | ND | 2.35 |
| N62D | S103A | V104I | S128G | G159D | T213R | A232V | Q236H | Q245R | N248D | N252K | | | 2.15 | 1.38 | ND | 1.77 |
| N62D | S103A | V104I | S128L | G159D | T213R | A232V | Q236H | Q245R | N248D | N252K | | | 3.07 | 0.07 | ND | 1.45 |
| S101G | S103A | V104I | P131V | G159D | A232V | Q236H | Q245R | N248D | N252K | | | | 2.26 | 1.16 | ND | 3.05 |
| A98V | S101G | S103A | V104I | G159D | A232V | Q236H | Q245R | N248D | N252K | | | | 1.82 | 1.34 | ND | 1.08 |
| S99G | S101G | S103A | V104I | G159D | A232V | Q236H | Q245R | N248D | N252K | | | | 2.16 | 1.47 | ND | 1.20 |
| S101G | S103A | V104I | G159D | S212G | A232V | Q236H | Q245R | N248D | N252K | | | | 1.79 | 1.38 | ND | 1.01 |
| S101G | S103A | V104I | G159D | Y209W | A232V | Q236H | Q245R | N248D | N252K | | | | 1.15 | 1.18 | ND | 8.7 |
| S101G | S103A | V104I | G159D | P210I | A232V | Q236H | Q245R | N248D | N252K | | | | 1.47 | 1.23 | ND | 1.03 |
| S101G | S103A | V104I | G159D | V2051 | A232V | Q236H | Q245R | N248D | N252K | | | | 1.90 | 1.38 | ND | 1.05 |

TABLE 6-continued

| | | | | | | | | | | | | | | | | |
|---|---|---|---|---|---|---|---|---|---|---|---|---|---|---|---|---|
| S101G | S103A | V104I | G159D | A230V | Q236H | Q245R | | | | | | | 1.55 | 1.51 | ND | 1.23 |
| S101G | S103A | V104I | G159D | A194P | A232V | Q236H | Q245R | N248D | N252K | | | | 1.96 | 1.30 | ND | 1.10 |
| N76D | S101G | S103A | V104I | G159D | A194P | A232V | Q236H | Q245R | N248D | N252K | | | 2.49 | 0.80 | ND | 1.25 |
| G61E | V68A | S103A | V104I | G159D | S160V | A232V | Q236H | Q245R | N248D | N252K | | | 420 | 7 | 128 | ND |
| S3L | G61E | V68A | N76D | S103A | V104I | A232V | Q236H | Q245R | N248D | N252K | | | 347 | 60 | 145 | ND |
| G61E | V68A | S103A | V104I | G159D | Y167F | A232V | Q236H | Q245R | N248D | N252K | | | 432 | 79 | 155 | ND |
| G97E | S103A | V104I | G159D | A232V | Q236H | Q245R | N248D | N252K | | | | | 314 | 41 | 140 | ND |
| A98D | S103A | V104I | G159D | A232V | Q236H | Q245R | N248D | N252K | | | | | 271 | 68 | 172 | ND |
| S99E | S103A | V104I | G159D | A232V | Q236H | Q245R | N248D | N252K | | | | | 297 | 68 | 171 | ND |
| S101E | S103A | V104I | G159D | A232V | Q236H | Q245R | N248D | N252K | | | | | 350 | 27 | 190 | ND |
| S101G | S103A | V104I | G159D | A232V | Q236H | Q245R | N248D | N252K | | | | | 224 | 180 | 133 | ND |
| G102A | S103A | V104I | G159D | A232V | Q236H | Q245R | N248D | N252K | | | | | 335 | 133 | 169 | ND |
| S103A | V104I | S106E | G159D | A232V | Q236H | Q245R | N248D | N252K | | | | | 488 | 55 | 271 | ND |
| S103A | V104I | Q109E | G159D | A232V | Q236H | Q245R | N248D | N252K | | | | | 422 | 105 | 240 | ND |
| S103A | V104I | G159D | A232V | Q236H | Q245R | N248D | N252K | N261R | | | | | 545 | 219 | 258 | ND |
| S103A | V104I | Q109R | G159D | A232V | Q236H | Q245R | N248D | N252K | | | | | 376 | 216 | 182 | ND |
| N62D | S103A | V104I | G159D | A232V | Q236H | Q245R | N248D | N252K | | | | | 742 | 13 | 246 | ND |
| S103A | V104I | G159D | N184D | A232V | Q236H | Q245R | N248D | N252K | | | | | 543 | 136 | 284 | ND |
| S103A | V104I | G159D | S166D | A232V | Q236H | Q245R | N248D | N252K | | | | | 512 | 121 | 397 | ND |
| S103A | V104I | G159D | L217E | A232V | Q236H | Q245R | N248D | N252K | | | | | 638 | 95 | 309 | ND |
| G20R | N62D | S103A | V104I | G159D | T213R | A232V | Q236H | Q245R | N248D | N252K | | | 317 | 283 | 260 | ND |
| N62D | S103A | V104I | G159D | T213R | A232V | Q236H | Q245R | N248D | N252K | | | | 438 | 192 | 254 | ND |
| S103A | V104I | G159D | Q206R | L217E | A232V | Q236H | Q245R | N248D | N252K | | | | 305 | 261 | 110 | ND |
| N62D | S103A | V104I | G159D | Q206R | A232V | Q236H | Q245R | N248D | N252K | | | | 409 | 246 | 255 | ND |
| S103A | V104I | G159D | N184G | A232V | Q236H | Q245R | N248D | N252K | | | | | 232 | 208 | 240 | ND |
| S103A | V104I | G159D | A232V | Q236H | V244T | Q245R | N248D | N252K | | | | | 234 | 204 | 186 | ND |
| S103A | V104I | G159D | A232V | Q236H | V244A | Q245R | N248D | N252K | | | | | 224 | 211 | 195 | ND |
| K27N | S103A | V104I | G159D | A232V | Q236H | Q245R | N248D | N252K | | | | | 281 | 156 | 247 | ND |
| T38G | S103A | V104I | G159D | A232V | Q236H | Q245R | N248D | N252K | | | | | 230 | 209 | 182 | ND |
| N62D | S103A | V104I | G159D | T213R | A232V | Q236H | Q245R | N248D | N252K | S256R | | | 263 | 266 | 144 | ND |
| Q12R | N62D | S103A | V104I | G159D | T213R | A232V | Q236H | Q245R | N248D | N252K | | | 201 | 278 | 199 | |
| N62D | S103A | V104I | G159D | N185D | Q206E | T213R | A232V | Q236H | Q245R | N248D | N252K | E271Q | 774 | 94 | 539 | ND |
| S101G | S103A | V104I | G159D | N185D | A232V | Q236H | Q245R | N248D | N252K | | | | 514 | 141 | 192 | ND |
| S101G | S103A | V104I | G159D | Q206E | A232V | Q236H | Q245R | N248D | N252K | | | | 497 | 57 | 136 | ND |
| S101G | S103A | V104I | G159D | T213Q | A232V | Q236H | Q245R | N248D | N252K | | | | 241 | 186 | 101 | ND |
| A98L | G102A | S103A | V104I | G159D | A232V | Q236H | Q245R | N248D | N252K | | | | 442 | 50 | 288 | ND |
| S101G | G102A | S103A | V104I | G159D | A232V | Q236H | Q245R | N248D | N252K | | | | 586 | 120 | 384 | ND |
| G102A | S103A | V104I | G159D | S212G | A232V | Q236H | Q245R | N248D | N252K | | | | 587 | 210 | 319 | ND |
| QI2R | G102A | S103A | V104I | G159D | S212G | A232V | Q236H | Q245R | N248D | N252K | | | 298 | 267 | 217 | ND |
| A98L | G102A | S103A | V104I | G159D | S212G | A232V | Q236H | Q245R | N248D | N252K | | | 402 | 41 | 225 | ND |
| S101G | G102A | S103A | V104I | G159D | S212G | A232V | Q236H | Q245R | N248D | N252K | | | 663 | 207 | 208 | ND |
| G102A | S103A | V104I | G159D | T213R | A232V | Q236H | Q245R | N248D | N252K | | | | 203 | 248 | 225 | ND |
| N62D | S103A | V104I | Q109R | G159D | T213R | A232V | Q236H | Q245R | N248D | N252K | | | 296 | 276 | 234 | ND |
| S103A | V104I | G159D | A232V | Q245R | N248D | N252K | | | | | | | 274 | 210 | 186 | ND |
| S103A | V104I | G159D | A230V | Q245R | | | | | | | | | 211 | 235 | 149 | ND |

TABLE 6-continued

| | | | | | | | | | | | | | | |
|---|---|---|---|---|---|---|---|---|---|---|---|---|---|---|
| N62D | S103A | V104I | S130G | G159D | T213R | A232V | Q236H | Q245R | N248D | N252K | 342 | 71 | 258 | ND |
| S101G | S103A | V104I | S130G | G159D | A232V | Q236H | Q245R | N248D | N252K | | 259 | 132 | 161 | ND |
| S101G | S103A | V104I | S128G | G159D | A232V | Q236H | Q245R | N248D | N252K | | 130 | 123 | 90 | ND |
| S101G | S103A | V104I | S128L | G159D | A232V | Q236H | Q245R | N248D | N252K | | 294 | 71 | 108 | ND |
| N62D | S101G | S103A | V104I | G159D | T213R | A232V | Q236H | Q245R | N248D | N252K | 317 | 83 | 235 | ND |
| N62D | S103A | V104I | S128G | G159D | T213R | A232V | Q236H | Q245R | N248D | N252K | 215 | 138 | 177 | ND |
| N62D | S103A | V104I | S128L | G159D | T213R | A232V | Q236H | Q245R | N248D | N252K | 307 | 7 | 145 | ND |
| S101G | S103A | V104I | PI3IV | G159D | A232V | Q236H | Q245R | N248D | N252K | | 226 | 116 | 305 | ND |
| A98V | S101G | S103A | V104I | G159D | A232V | Q236H | Q245R | N248D | N252K | | 182 | 134 | 108 | ND |
| S99G | S101G | S103A | V104I | G159D | A232V | Q236H | Q245R | N248D | N252K | | 216 | 147 | 120 | ND |
| S101G | S103A | V104I | G159D | S212G | A232V | Q236H | Q245R | N248D | N252K | | 179 | 138 | 101 | ND |
| S101G | S103A | V104I | G159D | Y209W | A232V | Q236H | Q245R | N248D | N252K | | 115 | 118 | 87 | ND |
| S101G | S103A | V104I | G159D | P210I | A232V | Q236H | Q245R | N248D | N252K | | 147 | 123 | 103 | ND |
| S101G | S103A | V104I | G1590 | V2051 | A232V | Q236H | Q245R | N248D | N252K | | 190 | 138 | 105 | ND |
| S101G | S103A | V104I | G159D | A230V | Q236H | Q245R | | | | | 155 | 151 | 123 | ND |
| S101G | S103A | V104I | G159D | A194P | A232V | Q236H | Q245R | N248D | N252K | | 196 | 130 | 110 | ND |
| N76D | S101G | S103A | V104I | G159D | A232V | Q236H | Q245R | N248D | N252K | | 249 | 80 | 125 | ND |

What is claimed:

1. A protease variant comprising replacing an amino acid at the residue position corresponding to residue position 232 of the *Bacillus amyloliquifaciens* subtilisin.

2. The protease variant of claim 1, wherein said variant is A232V.

3. The protease variant of claim 1 further including, substitution of the amino acid residue at one or both of positions 62 and 230.

4. The protease variant of claim 1 further including, substituting one or more amino acids at residue positions selected from the group consisting of residue positions corresponding to positions 1, 9, 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270, and 275 of the *Bacillus amyloliquifaciens* subtilisin.

5. The protease variant of claim 1 further comprising, substituting an amino acid residue at residue position corresponding to position 103 of the *Bacillus amyloliquifaciens* subtilisin.

6. The protease variant of claim 1 further comprising, substituting an amino acid residue at residue position corresponding to position 104 of the *Bacillus amyloliquifaciens* subtilisin.

7. The protease variant of claim 5 further comprising, substituting an amino acid residue at residue position corresponding to position 104 of the *Bacillus amyloliquifaciens* subtilisin.

8. The protease variant of claim 1 further comprising, substituting an amino acid residue at residue position corresponding to position 236 of the *Bacillus amyloliquifaciens* subtilisin.

9. The protease variant of claim 1 further comprising, substituting an amino acid residue at residue position corresponding to position 245 of the *Bacillus amyloliquifaciens* subtilisin.

10. The protease variant of claim 1 further comprising, substituting an amino acid residue at residue position corresponding to position 252 of the *Bacillus amyloliquifaciens* subtilisin.

11. The protease variant of claim 1 further comprising, substituting an amino acid residue at residue position corresponding to position 257 of the *Bacillus amyloliquifaciens* subtilisin.

12. The protease variant of claim 1 further including, substituting one or more amino acids at residue positions selected from the group consisting of residue positions corresponding to positions 101, 103, 104, 159, 236, and 248 of the *Bacillus amyloliquifaciens* subtilisin.

13. The protease variant of claim 1 further including, substituting one or more amino acids at residue positions selected from the group consisting of residue positions corresponding to positions 101, 103, 104, 159, 236, 245, 248 and 252 of the *Bacillus amyloliquifaciens* subtilisin.

14. A protease variant comprising replacing the amino acid at the residue position corresponding to position 212 of the *Bacillus amyloliquifaciens* subtilisin with a proline, wherein said variant is a substitution set selected from the group consisting of N76D/S103A/V104I/S212P/E271V; N76D/S103A/V104I/S212P/G258R; N76D/S103A/V104I/S212P/V268F/E271V; N76D/S87R/S103A/V104I/S212P/E271V; and N76D/S103A/V104I/T134S/S141N/S212P/E271V.

15. The protease variant according to claim 1, which is derived from a Bacillus subtilisin.

16. The protease variant according to claim 15 which is derived from *Bacillus lentus* subtilisin.

17. A DNA encoding a protease variant of claim 1.

18. An expression vector encoding the DNA of claim 1.

19. A host cell transformed with the expression vector of claim 18.

20. A cleaning composition comprising the protease variant of claim 1.

21. An animal feed comprising the protease variant of claim 1.

22. A composition for treating a textile comprising the protease variant of claim 1.

* * * * *

SEQUENCE LISTING

```
<160> NUMBER OF SEQ ID NOS: 6

<210> SEQ ID NO 1
<211> LENGTH: 1497
<212> TYPE: DNA
<213> ORGANISM: B. amyloliquefaciens
<220> FEATURE:
<221> NAME/KEY: CDS
<222> LOCATION: (96)...(1245)

<400> SEQUENCE: 1

ggtctactaa aatattattc catactatac aattaataca cagaataatc tgtctattgg      60

ttattctgca aatgaaaaaa aggagaggat aaaga gtg aga ggc aaa aaa gta        113
                                       Met Arg Gly Lys Lys Val
                                        1               5

tgg atc agt ttg ctg ttt gct tta gcg tta atc ttt acg atg gcg ttc       161
Trp Ile Ser Leu Leu Phe Ala Leu Ala Leu Ile Phe Thr Met Ala Phe
            10                  15                  20

ggc agc aca tcc tct gcc cag gcg gca ggg aaa tca aac ggg gaa aag       209
Gly Ser Thr Ser Ser Ala Gln Ala Ala Gly Lys Ser Asn Gly Glu Lys
        25                  30                  35

aaa tat att gtc ggg ttt aaa cag aca atg agc acg atg agc gcc gct       257
Lys Tyr Ile Val Gly Phe Lys Gln Thr Met Ser Thr Met Ser Ala Ala
    40                  45                  50

aag aag aaa gat gtc att tct gaa aaa ggc ggg aaa gtg caa aag caa       305
Lys Lys Lys Asp Val Ile Ser Glu Lys Gly Gly Lys Val Gln Lys Gln
 55                  60                  65                  70

ttc aaa tat gta gac gca gct tca gtc aca tta aac gaa aaa gct gta       353
Phe Lys Tyr Val Asp Ala Ala Ser Val Thr Leu Asn Glu Lys Ala Val
                75                  80                  85

aaa gaa ttg aaa aaa gac ccg agc gtc gct tac gtt gaa gaa gat cac       401
Lys Glu Leu Lys Lys Asp Pro Ser Val Ala Tyr Val Glu Glu Asp His
            90                  95                 100

gta gca cat gcg tac gcg cag tcc gtg cct tac ggc gta tca caa att       449
Val Ala His Ala Tyr Ala Gln Ser Val Pro Tyr Gly Val Ser Gln Ile
        105                 110                 115

aaa gcc cct gct ctg cac tct caa ggc tac act gga tca aat gtt aaa       497
Lys Ala Pro Ala Leu His Ser Gln Gly Tyr Thr Gly Ser Asn Val Lys
    120                 125                 130

gta gcg gtt atc gac agc ggt atc gat tct tct cat cct gat tta aag       545
Val Ala Val Ile Asp Ser Gly Ile Asp Ser Ser His Pro Asp Leu Lys
135                 140                 145                 150

gta gca agc gga gcc agc atg gtt cct tct gaa aca aat cct ttc caa       593
Val Ala Ser Gly Ala Ser Met Val Pro Ser Glu Thr Asn Pro Phe Gln
                155                 160                 165

gac aac aac tct cac gga act cac gtt gcc ggc aca gtt gcg gct ctt       641
Asp Asn Asn Ser His Gly Thr His Val Ala Gly Thr Val Ala Ala Leu
            170                 175                 180

aat aac tca atc ggt gta tta ggc gtt gcg cca agc gca tca ctt tac       689
Asn Asn Ser Ile Gly Val Leu Gly Val Ala Pro Ser Ala Ser Leu Tyr
        185                 190                 195

gct gta aaa gtt ctc ggt gct gac ggt tcc ggc caa tac agc tgg atc       737
Ala Val Lys Val Leu Gly Ala Asp Gly Ser Gly Gln Tyr Ser Trp Ile
    200                 205                 210

att aac gga atc gag tgg gcg atc gca aac aat atg gac gtt att aac       785
Ile Asn Gly Ile Glu Trp Ala Ile Ala Asn Asn Met Asp Val Ile Asn
215                 220                 225                 230

atg agc ctc ggc gga cct tct ggt tct gct gct tta aaa gcg gca gtt       833
Met Ser Leu Gly Gly Pro Ser Gly Ser Ala Ala Leu Lys Ala Ala Val
```

-continued

```
                235                 240                 245

gat aaa gcc gtt gca tcc ggc gtc gta gtc gtt gcg gca gcc ggt aac      881
Asp Lys Ala Val Ala Ser Gly Val Val Val Val Ala Ala Ala Gly Asn
            250                 255                 260

gaa ggc act tcc ggc agc tca agc aca gtg ggc tac cct ggt aaa tac      929
Glu Gly Thr Ser Gly Ser Ser Ser Thr Val Gly Tyr Pro Gly Lys Tyr
        265                 270                 275

cct tct gtc att gca gta ggc gct gtt gac agc agc aac caa aga gca      977
Pro Ser Val Ile Ala Val Gly Ala Val Asp Ser Ser Asn Gln Arg Ala
    280                 285                 290

tct ttc tca agc gta gga cct gag ctt gat gtc atg gca cct ggc gta     1025
Ser Phe Ser Ser Val Gly Pro Glu Leu Asp Val Met Ala Pro Gly Val
295                 300                 305                 310

tct atc caa agc acg ctt cct gga aac aaa tac ggg gcg tac aac ggt     1073
Ser Ile Gln Ser Thr Leu Pro Gly Asn Lys Tyr Gly Ala Tyr Asn Gly
                315                 320                 325

acg tca atg gca tct ccg cac gtt gcc gga gcg gct gct ttg att ctt     1121
Thr Ser Met Ala Ser Pro His Val Ala Gly Ala Ala Ala Leu Ile Leu
            330                 335                 340

tct aag cac ccg aac tgg aca aac act caa gtc cgc agc agt tta gaa     1169
Ser Lys His Pro Asn Trp Thr Asn Thr Gln Val Arg Ser Ser Leu Glu
        345                 350                 355

aac acc act aca aaa ctt ggt gat tct ttg tac tat gga aaa ggg ctg     1217
Asn Thr Thr Thr Lys Leu Gly Asp Ser Leu Tyr Tyr Gly Lys Gly Leu
    360                 365                 370

atc aac gta caa gcg gca gct cag taa a acataaaaaa ccggccttgg         1265
Ile Asn Val Gln Ala Ala Ala Gln
375                 380

ccccgccggt tttttattat ttttcttcct ccgcatgttc aatccgctcc ataatcgacg   1325

gatggctccc tctgaaaatt ttaacgagaa acggcgggtt gacccggctc agtcccgtaa   1385

cggccaactc ctgaaacgtc tcaatcgccg cttcccggtt tccggtcagc tcaatgccat   1445

aacggtcggc ggcgttttcc tgataccggg agacggcatt cgtaatcgga tc           1497


<210> SEQ ID NO 2
<211> LENGTH: 382
<212> TYPE: PRT
<213> ORGANISM: B. amyloliquefaciens

<400> SEQUENCE: 2

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Val Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
```

-continued

```
    130                 135                 140

Ser His Pro Asp Leu Lys Val Ala Ser Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Leu
        355                 360                 365

Tyr Tyr Gly Lys Gly Leu Ile Asn Val Gln Ala Ala Ala Gln
    370                 375                 380


<210> SEQ ID NO 3
<211> LENGTH: 275
<212> TYPE: PRT
<213> ORGANISM: B. amyloliquefaciens

<400> SEQUENCE: 3

Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125
```

-continued

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 4
<211> LENGTH: 275
<212> TYPE: PRT
<213> ORGANISM: B. subtilis

<400> SEQUENCE: 4

Ala Gln Ser Val Pro Tyr Gly Ile Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

-continued

Pro His Val Ala Gly Ala Ala Ala Leu Ile Leu Ser Lys His Pro Thr
225 230 235 240

Trp Thr Asn Ala Gln Val Arg Asp Arg Leu Glu Ser Thr Ala Thr Tyr
245 250 255

Leu Gly Asn Ser Phe Tyr Tyr Gly Lys Gly Leu Ile Asn Val Gln Ala
260 265 270

Ala Ala Gln
275

<210> SEQ ID NO 5
<211> LENGTH: 274
<212> TYPE: PRT
<213> ORGANISM: B. licheniformis

<400> SEQUENCE: 5

Ala Gln Thr Val Pro Tyr Gly Ile Pro Leu Ile Lys Ala Asp Lys Val
1 5 10 15

Gln Ala Gln Gly Phe Lys Gly Ala Asn Val Lys Val Ala Val Leu Asp
20 25 30

Thr Gly Ile Gln Ala Ser His Pro Asp Leu Asn Val Val Gly Gly Ala
35 40 45

Ser Phe Val Ala Gly Glu Ala Tyr Asn Thr Asp Gly Asn Gly His Gly
50 55 60

Thr His Val Ala Gly Thr Val Ala Ala Leu Asp Asn Thr Thr Gly Val
65 70 75 80

Leu Gly Val Ala Pro Ser Val Ser Leu Tyr Ala Val Lys Val Leu Asn
85 90 95

Ser Ser Gly Ser Gly Ser Tyr Ser Gly Ile Val Ser Gly Ile Glu Trp
100 105 110

Ala Thr Thr Asn Gly Met Asp Val Ile Asn Met Ser Leu Gly Gly Ala
115 120 125

Ser Gly Ser Thr Ala Met Lys Gln Ala Val Asp Asn Ala Tyr Ala Arg
130 135 140

Gly Val Val Val Val Ala Ala Ala Gly Asn Ser Gly Asn Ser Gly Ser
145 150 155 160

Thr Asn Thr Ile Gly Tyr Pro Ala Lys Tyr Asp Ser Val Ile Ala Val
165 170 175

Gly Ala Val Asp Ser Asn Ser Asn Arg Ala Ser Phe Ser Ser Val Gly
180 185 190

Ala Glu Leu Glu Val Met Ala Pro Gly Ala Gly Val Tyr Ser Thr Tyr
195 200 205

Pro Thr Asn Thr Tyr Ala Thr Leu Asn Gly Thr Ser Met Ala Ser Pro
210 215 220

His Val Ala Gly Ala Ala Ala Leu Ile Leu Ser Lys His Pro Asn Leu
225 230 235 240

Ser Ala Ser Gln Val Arg Asn Arg Leu Ser Ser Thr Ala Thr Tyr Leu
245 250 255

Gly Ser Ser Phe Tyr Tyr Gly Lys Gly Leu Ile Asn Val Glu Ala Ala
260 265 270

Ala Gln

<210> SEQ ID NO 6
<211> LENGTH: 269
<212> TYPE: PRT
<213> ORGANISM: B. lentus

-continued

```
<400> SEQUENCE: 6

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```